(12) United States Patent
Schweizer et al.

(10) Patent No.: US 11,998,560 B2
(45) Date of Patent: Jun. 4, 2024

(54) **POTENTIATION OF β-LACTAM ANTIBIOTICS AND β-LACTAM/β-LACTAMASE INHIBITOR COMBINATIONS AGAINST MULTIDRUG AND EXTENSIVELY DRUG-RESISTANT *PSEUDOMONAS AERUGINOSA* USING NON-RIBOSOMAL TOBRAMYCIN-CYCLAM CONJUGATES**

(71) Applicant: University of Manitoba, Winnipeg (CA)

(72) Inventors: Frank Schweizer, Winnipeg (CA); Temilolu Idowu, Winnipeg (CA); Derek Ammeter, Winnipeg (CA)

(73) Assignee: University of Manitoba, Winnipeg (CA)

( * ) Notice: Subject to any disclaimer, the term of this patent is extended or adjusted under 35 U.S.C. 154(b) by 456 days.

(21) Appl. No.: 17/266,219

(22) PCT Filed: Nov. 22, 2019

(86) PCT No.: PCT/CA2019/051675
§ 371 (c)(1),
(2) Date: Feb. 5, 2021

(87) PCT Pub. No.: WO2020/102910
PCT Pub. Date: May 28, 2020

(65) Prior Publication Data
US 2021/0290648 A1 Sep. 23, 2021

Related U.S. Application Data

(60) Provisional application No. 62/770,929, filed on Nov. 23, 2018.

(51) Int. Cl.
*A61K 31/7036* (2006.01)
*A61K 31/407* (2006.01)
*A61K 31/427* (2006.01)
*A61K 31/43* (2006.01)
*A61K 31/545* (2006.01)
*A61K 47/54* (2017.01)
*A61P 31/04* (2006.01)
*C07H 15/26* (2006.01)

(52) U.S. Cl.
CPC ........ *A61K 31/7036* (2013.01); *A61K 31/407* (2013.01); *A61K 31/427* (2013.01); *A61K 31/43* (2013.01); *A61K 31/545* (2013.01); *A61K 47/547* (2017.08); *A61P 31/04* (2018.01); *C07H 15/26* (2013.01)

(58) Field of Classification Search
CPC .............. C07H 15/234; A61K 31/7036; A61K 47/547; A61P 31/04
See application file for complete search history.

(56) References Cited

PUBLICATIONS

Allam et al., European Journal of Medicinal Chemistry, 2017, 127, p. 748-756. (Year: 2017).*

* cited by examiner

*Primary Examiner* — Jonathan S Lau
(74) *Attorney, Agent, or Firm* — Michael R. Williams; Kyle R. Satterthwaite; Ade & Company Inc.

(57) ABSTRACT

Herein, we describe the development of non-β-lactam-based potentiator molecules that synergize with β-lactam antibiotics and β-lactam-β-lactamase inhibitor combinations against MDR/XDR *P. aeruginosa* phenotypes. The compound comprises a chemical structure or chemical formula of Formula (A) or a suitable salt form thereof, wherein "n" is a carbon tether having a length of between about 2-18 carbons.

12 Claims, 13 Drawing Sheets a)

b)

a)

b)

a)

b)

a)

b)

a)

b)

c)

a)

b)

POTENTIATION OF β-LACTAM ANTIBIOTICS AND β-LACTAM/β-LACTAMASE INHIBITOR COMBINATIONS AGAINST MULTIDRUG AND EXTENSIVELY DRUG-RESISTANT *PSEUDOMONAS AERUGINOSA* USING NON-RIBOSOMAL TOBRAMYCIN-CYCLAM CONJUGATES

PRIOR APPLICATION INFORMATION

The instant application is a 371 of PCT Patent Application PCT CA2019/051675, filed Nov. 22, 2019, now abandoned, which claimed the benefit of U.S. Provisional Patent Application 62/770,929, filed Nov. 23, 2018, and entitled "Potentiation of β-Lactam Antibiotics and β-Lactam/β-Lactamase Inhibitor Combinations against Multidrug and Extensively Drug-resistant *Pseudomonas aeruginosa* using Non-ribosomal Tobramycin-Cyclam Conjugates", the entire contents of which are incorporated herein by reference for all purposes.

BACKGROUND OF THE INVENTION

There is consensus in the scientific community, and a growing awareness in general society, that antimicrobial resistance constitutes a serious threat to the expected standard of medical care. The emergence of carbapenem-resistant Gram-negative bacteria is considered a public health crisis and a major global threat to all the clinical procedures that rely on effective antibiotic therapy (1, 2). Carbapenem resistance in Gram-negative pathogens is almost always associated with resistance to several other classes of antibiotics because carbapenemase-encoding genes are located on mobile genetic elements that frequently carry genes responsible for resistance to other antibiotics (3, 4). Thus, these phenotypes are frequently multidrug-resistant (MDR, i.e. non-susceptibility to at least one agent in at least three antimicrobial categories), extensively drug-resistant (XDR, i.e. non-susceptibility to at least one agent in all but two or fewer antimicrobial categories), and in some cases, pan-drug-resistant (PDR, i.e. non-susceptibility to all categories of antimicrobial agents) (5).

Gram-negative bacteria are intrinsically resistant to many antibiotics because of their protective outer membrane (OM) barrier that prevents the passage of potentially noxious molecules into the cell without compromising the exchange of materials required for sustaining life (6). The cellular and molecular basis for the integrity of the OM, an asymmetric bilayer of lipopolysaccharides (LPS) and phospholipids, lie in the efficient packing of the lipid A component of LPS (6). This packing ensures a lower fluidity of the OM which in turn limits the passage and permeation of hydrophobic agents. However, the antimicrobial susceptibility patterns of *Pseudomonas aeruginosa*, a versatile opportunistic pathogen and a leading cause of nosocomial infections in debilitated patients (7), differ in many respects from those of other Gram-negative bacteria. For instance, the OM of *P. aeruginosa* is even less permeable (approximately 8% that of *Escherichia coli*) as the organism regulates the lipid A component of its LPS differently from other Gram-negative pathogens (8, 9). This, coupled with its overexpressed efflux pumps of broad substrate specificities and highly efficient adaptive machinery (10-12), confer a multimodal sophisticated mechanism of resistance on *P. aeruginosa*. Indeed, *P. aeruginosa* is well known for its ability to evade antibiotic activity (11-14). Therefore, the ability to permeabilize the OM of *P. aeruginosa* should, in principle, make the pathogen more vulnerable to agents that are otherwise inactive against it. Even for compounds with porin-mediated uptake such as β-lactams, tetracyclines, and fluoroquinolones (15), destabilization of the OM could ensure that the rate of drug influx into the cell overwhelms the rate of active extrusion, thereby enhancing antibiotic accumulation.

Aminoglycosides (AGs) are a unique class of antipseudomonal agents in that they can promote their own uptake via a mechanism that is independent of porin channels. They perturb the OM of Gram-negative bacteria by displacing the stabilizing divalent cations that cross-bridge adjacent LPS in a concentration-dependent manner, known as the self-promoted uptake mechanism, and they traverse the inner membrane via an energy-dependent process (16). At lower concentrations (i.e. <4 μg/mL), AGs interfere with the fidelity of ribosomal protein translation while they are believed to disrupt the OM at higher concentrations (i.e. ≥8 μg/mL) (17). One consequence of the ribosomal effects of AGs, is that it easily selects for resistant genotypes and phenotypes (18, 19). To exploit the unique concentration-dependent properties of this class of drugs without necessarily generating resistant phenotypes, it has previously been shown that specific modifications and systematic conjugation to other moieties can decouple the OM effects of AGs from their ribosomal functions (13, 20, 21). This means that a non-ribosomal AG may not trigger a direct response mechanism in bacteria but can still induce a self-promoted uptake and disrupt the OM. Specifically, the OM permeabilizing properties of non-ribosomal tobramycin conjugates were 100- to 1000-fold higher than that of tobramycin by itself, and were found to potentiate the effects of several OM-impermeable antibiotics including rifampicin, vancomycin, and novobiocin against *P. aeruginosa* (13, 20, 22). For example, a tobramycin-ciprofloxacin hybrid (at ≤1 μg/mL) potentiated rifampicin and novobiocin against *P. aeruginosa* PAO1 by 128-fold and 512-fold, respectively, while tobramycin by itself does not (20). These conjugates were also found to dissipate the cytoplasmic proton-motive force that energizes efflux pumps (13, 20, 22, 23).

β-Lactam antibiotics (monobactams, penicillins, cephalosporins, and carbapenems) are cornerstone agents and an integral part of the treatment of Gram-negative bacterial infections, especially against *P. aeruginosa* for which treatment options are limited. They are the most widely used group of antibiotics and they exhibit their bactericidal effects by binding to the penicillin binding proteins (PBPs) involved in cell wall synthesis. Unfortunately, primary mechanisms of resistance such as changes in the active site of PBPs, decreased expression of OM porin proteins, augmented antibiotic efflux, and the dissemination of β-lactamase-encoding genes have threatened the continuous use of this highly important class of antibiotics from an already shrinking antibiotic arsenal (24). To preserve the therapeutic relevance of β-lactam antibiotics, efforts have focused more on developing newer generations that can withstand enzymatic degradation and/or develop partner molecules that could shield the β-lactam core from enzymatic inactivation, as evident in the recent approvals of ceftolozane-tazobactam (2014), ceftazidime-avibactam (2015), and meropenem-vaborbactam (2017) combinations by the FDA. However, complete loss or diminished expression of the OprD and OprF OM proteins, especially in *P. aeruginosa* that can survive utilizing other protein channels (7-9), can bestow microbiological resistance to both β-lactam antibiotics and β-lactamase inhibitors. Indeed, reduced expression of the OprD OM protein, a common channel for uptake of basic amino acids and small peptides that share structural similarities with carbapenems, has been found to confer low level resistance to carbapenems on *P. aeruginosa* (25, 26). Whereas basic amino acids induce up-regulation of OprD protein expression, trace metals such as zinc and copper have been shown to induce decreased OprD expression in *P. aeruginosa* via two-component regulators, CzcR-CzcS and copR-copS regulatory systems, respectively (27-29).

SUMMARY OF THE INVENTION

According to an aspect of the invention, there is provided a compound comprising a chemical structure or chemical formula of Formula (A):

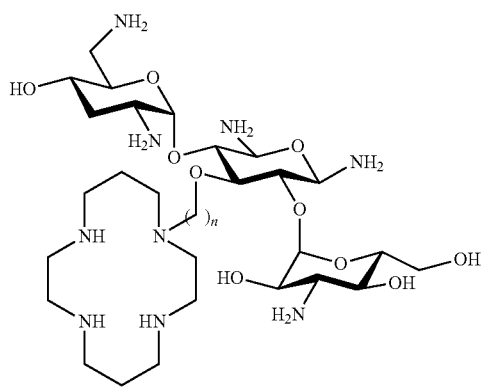

(A)

or a suitable salt form thereof, wherein "n" is a carbon tether having a length of between about 2-18 carbons.

As discussed herein, "carbon tether" does not mean that the tether must be composed of only carbon atoms, but rather a tether that has a length similar or approximate to that of 2-18 carbons. For example, the carbon tether could contain polyethyleneglycol units (O—CH2-CH2)n (n=1-10).

According to another aspect of the invention, there is provided a compound comprising a chemical structure or chemical formula of formula (I)

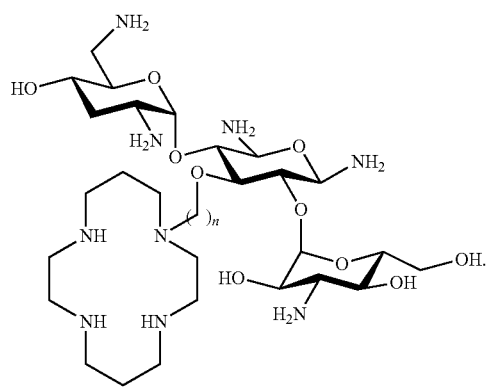

(I)

1: n = 4 (X 9TFA)
2: n = 8 (X 9TFA)
3: n = 12 (X 9HCl)

or a suitable salt form thereof.

According to a further aspect of the invention, there is provided a compound consisting of a chemical structure or chemical formula of formula (I)

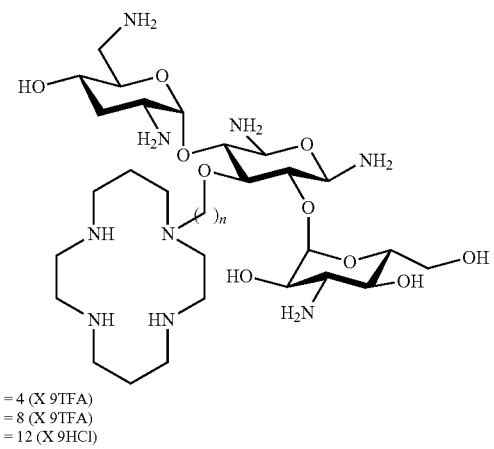

(I)

1: n = 4 (X 9TFA)
2: n = 8 (X 9TFA)
3: n = 12 (X 9HCl)

or a suitable salt form thereof.

It is to be understood that while the above formulae make reference to trifluoroacetic acid (TFA) salts with respect to compounds with n=4 or n=8 as the tether and hydrochloric acid (HCl) salt with respect to n=12 as the tether, the formula (I) is intended to represent both neutral and suitable salt forms of the compound. It should further be noted that TFA and HCl represent two exemplary examples of suitable salts, others of which will be readily apparent to one of skill in the art.

According to another aspect of the invention, there is provided a method of perturbing or permeabilizing or destabilizing or increasing the fluidity of the outer membrane of a gram-negative bacterium comprising: administering to an individual in need of such treatment an effective amount of compound comprising a chemical structure of Formula (A), as set forth above.

According to yet another aspect of the invention, there is provided use of a compound for perturbing or permeabilizing or destabilizing or increase the fluidity of the outer membrane of a gram-negative bacterium, said compound comprising the chemical structure of Formula (A), as set forth above.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

The emergence of carbapenem-resistant Gram-negative bacteria marked a watershed in our long struggle against antimicrobial resistance. Current strategies to mitigate this problem are geared towards developing inhibitors that can shield β-lactam antibiotics from enzymatic inactivation by β-lactamases. However, complete loss or diminished expression of OprD and OprF porins has been a consistent phenomenon in *P. aeruginosa* phenotypes that are microbiologically resistant to β-lactam antibiotics. Herein, we describe the development of non-β-lactam-based potentiator molecules that synergize with β-lactam antibiotics and β-lactam-β-lactamase inhibitor combinations against MDR/XDR *P. aeruginosa* phenotypes. In combination with <10 μM of this adjuvant, aztreonam and meropenem display growth-inhibition against resistant isolates at levels equal or below their corresponding clinical breakpoints. Time-kill kinetics reveal a dose-dependent pharmacodynamic relationship, and a combination of the adjuvant with aztreonam, meropenem, or ceftazidime display efficacy against MDR *P. aeruginosa* in vivo at clinically relevant doses. A triple combination of the adjuvant with ceftazidime-avibactam (FDA-approved), aztreonam-avibactam (in Phase III clinical trials), or meropenem-avibactam enhances the therapeutic efficacies of these β-lactam/β-lactamase inhibitor combinations in vitro and in vivo. β-Lactamases are typically found in the periplasmic space of Gram-negative bacteria, and the rapidity with which inhibitors can access their targets is critical for successful inhibition. As discussed below, taken together, our data indicates that tobramycin-cyclam conjugates can overcome resistance to β-lactam antibiotics and enhance the activity and efficacy of β-lactam/β-lactamase inhibitor combinations by permeabilizing the outer membrane of recalcitrant pathogens such as *P. aeruginosa*, one of the most common and feared pathogens in hospitals.

Figure 1:
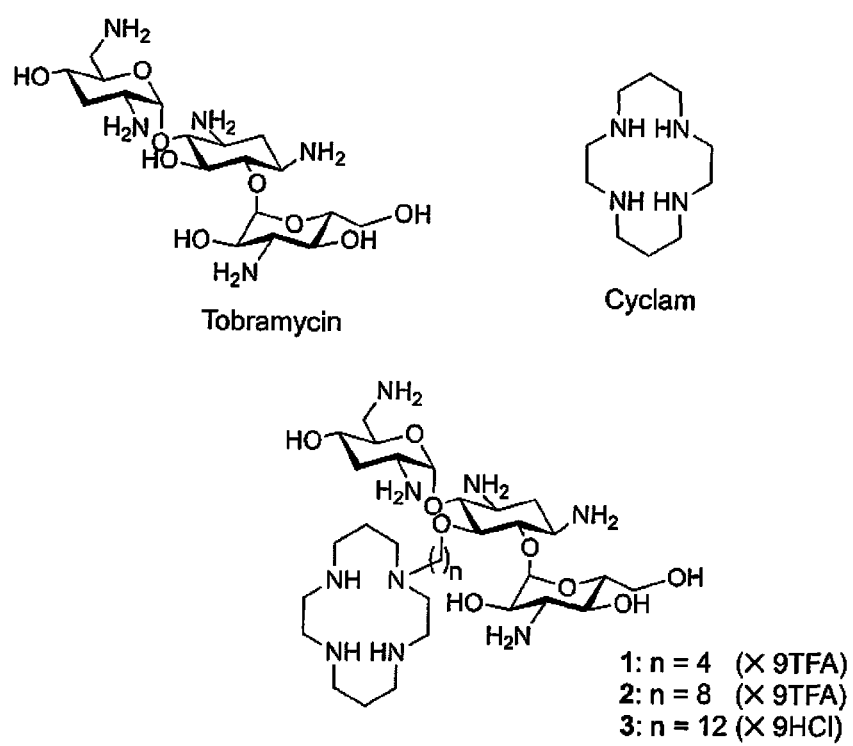
FIG. 1: Structures of Tobramycin, Cyclam, and newly synthesized Tobramycin-Cyclam conjugates 1-3. Conjugates differ in the length of carbon chains. Compound 3 was converted to HCl salt by treating the TFA salt form with a stoichiometric amount of aqueous HCl solution.

Described herein is the development of a classic antibiotic adjuvant that combines the membrane-permeabilizing properties of a non-ribosomal amphiphilic tobramycin on one hand with a metal-chelating property of a secondary moiety on the other hand. A chelating agent may not only disrupt the OM of Gram-negative bacteria by sequestering the stabilizing divalent metals (K),[30] it may also prevent downregulation of the OprD proteins by chelating divalent metals needed by CzcR-CzcS/copR-copS two-component regulatory systems (27-29). Moreover, intracellular metal ions such as $Zn^{2+}$ that activate nucleophilic water molecules are used by metallo-β-lactamase enzymes to hydrolyze carbapenems. For example, aspergillomarasmine A was shown to reverse carbapenem resistance by chelating the divalent zinc metal used by these enzymes to hydrolyze carbapenems (31). Cyclam (1,4,8,11-tetraazacyclotetradecane), a macrocyclic polyamine (FIG. 1), was selected as the investigative metal-chelating agent because of its non-toxic properties towards eukaryotic cells, well-known coordination chemistry with divalent metals, tractable synthetic handling, and the biological activities of its complexes are well documented (32, 33). Moreover, a lipophilic cationic neamine grafted to a cyclam domain was found to permeabilize the OM of an MDR *Enterobacter aerogenes* (34). Herein, we report the design, synthesis and evaluation of a series of non-ribosomal, non-toxic tobramycin-cyclam conjugates shown generally by Formula (A), specific exemplary examples of which include compounds 1-3 (FIG. 1) that rescue the efficacy of β-lactam antibiotics against MDR/XDR *P. aeruginosa* in vitro and in vivo. We show that these conjugates are inactive as standalone agents but when used in combination with β-lactam antibiotics, organism MICs were reduced such that CLSI susceptibility breakpoints were reached for aztreonam in seven out of nine aztreonam-resistant *P. aeruginosa* clinical isolates, and for meropenem in eight out of nine carbapenem-resistant isolates. We also show that these non-ribosomal tobramycin conjugates potentiate the effects of β-lactam/β-lactamase inhibitor combinations against five out of five β-lactamase-producing MDR *P. aeruginosa* in vitro and in vivo. These synergistic effects are dose-dependent and were more pronounced in *P. aeruginosa* than in other Gram-negative bacteria. The absolute MICs of hydrophobic OM-impermeable antibiotics such as rifampicin, novobiocin, chloramphenicol, erythromycin, etc. were significantly reduced to clinically-relevant concentrations in the presence of these tobramycin-cyclam conjugates, an indication of OM permeabilization that consequently facilitates the uptake of OM-impermeable antibiotics.

A consistent finding in carbapenem-resistant isolates has been the loss of OprD porins, and a reduction in the OM protein OprF in *P. aeruginosa* has been associated with resistance to aztreonam and ceftazidime (26, 43). In this study, we have shown that non-ribosomal tobramycin-cyclam conjugates, designed as a classic OM permeabilizer, rescue the potency of aztreonam and meropenem against resistant *P. aeruginosa* phenotypes in vitro and in vivo. We have also demonstrated the therapeutic advantage of a triple combination of β-lactam antibiotics+β-lactamase inhibitor+compound 2 over the conventional β-lactam antibiotics+β-lactamase inhibitor, in vitro and in vivo. β-Lactam antibiotics are core to anti-pseudomonal drug regimens and they are the most effective class of drug used in combination therapy to treat multidrug resistant Gram-negative bacteria infections.

Figure 2:
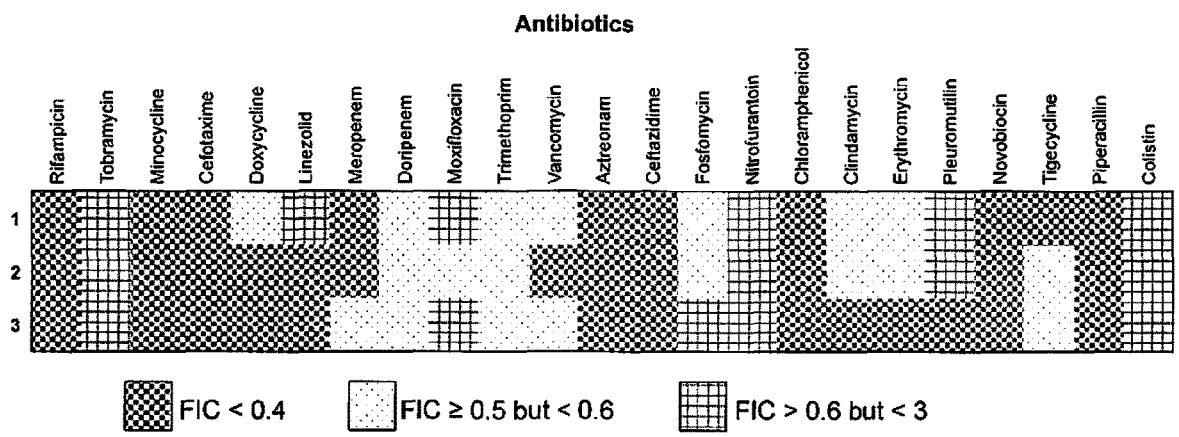
FIG. 2. (a) Interactions of compounds 1-3 (at ≤10 μM, i.e. 2-16 μg/ml) with different antibiotics against WT *P. aeruginosa* PAO1. FIC<0.4=Green; FIC≥0.5 but<0.6=Yellow; FIC>0.6 but<3=Red, (b) Fold potentiation of several classes of antibiotics by tobramycin-cyclam conjugates 1-3 (at ≤10 μM) against WT *P. aeruginosa* PAO1
Figure 2:
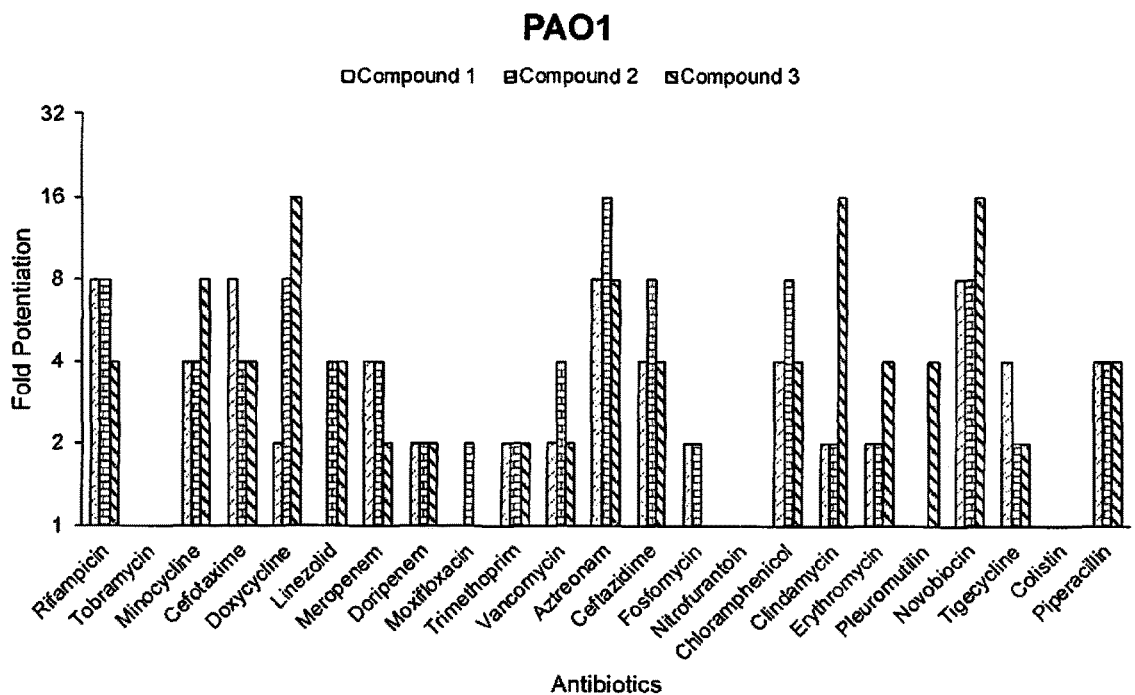

The dearth of novel antibacterial drugs in the pipeline means that we must conserve the efficacy of existing antibacterial drugs as much as practically possible. β-Lactam antibiotics are important agents for preventing and treating life-threatening nosocomial infections which are often associated with debilitated patients and/or techniques developed in modern medicine (transplantation, hospitalization in intensive care units, surgery) (56). Sadly, the global dissemination of β-lactamases (Ambler classes A-D) and adaptive bacteria responses such as loss of porin channels and over-expression of efflux proteins is a threat to the continued clinical utility of β-lactam antibiotics (24). With no reprieve in sight, the pursuit of adjuvants that can inhibit the actions of β-lactamases and/or reverse intrinsic/adaptive resistance is critical for the survival of β-lactam antibiotics. There are currently several FDA-approved adjuvants for β-lactams antibiotics that prevent/inhibit enzymatic inactivation, but none, to our knowledge, has been approved to enhance permeation across porin-deficient phenotypes Non-ribosomal tobramycin-cyclam conjugates were conceptualized and designed to combine the OM-permeabilizing properties of an amphiphilic aminoglycoside with the chelating properties of a cyclam domain, with a view of destabilizing the OM of *P. aeruginosa* and possibly inhibiting the actions of class B β-lactamase enzymes (metallo-β-lactamases) that require zinc to be active 956). Amphiphilic tobramycins conjugated in this fashion are unable to bind to 16S rRNA (35) but can bind to LPS and induce *P. aeruginosa* membrane depolarization (57). The results of this design are molecules that do not possess intrinsic antimicrobial activities by themselves (Table 1) but potentiate the effects of other antibiotics (FIG. 2). Interestingly, the newly synthesized compounds 1-3 synergized with OM-impermeable hydrophobic compounds such as rifampicin and novobiocin but only marginally with the hydrophilic glycopeptide vancomycin (FIG. 2 and Table 2). Similar to SPR741 (59), pentamidine is unable to potentiate rifampicin against *P. aeruginosa* (58). There is a history of β-lactam/AG synergism in *P. aeruginosa* but this interaction is due to the intrinsic activities of the individual antibiotics (45, 52, 60, 61). The underlying mechanism of interaction between these agents is believed to be the destruction of cell wall peptidoglycan polymers by β-lactams, thus, facilitating the uptake/entry of AGs that subsequently exert their bactericidal effects by disrupting the cytoplasmic membrane. The lack of potent antibacterial activities of compounds 1-3 against both Gram-positive and Gram-negative bacteria, as well as against tobramycin-susceptible and tobramycin-resistant *P. aeruginosa* phenotypes (Table 1), shows that the synergistic interactions between compound 2 and β-lactam antibiotics is not due to the intrinsic activity of the tobramycin domain. Moreover, the in vitro effects of β-lactam/tobramycin interactions against wildtype and MDR/XDR *P. aeruginosa* were only marginally additive at therapeutic concentrations. Tobramycin has been identified as an exception to β-lactam/AG synergism in *P. aeruginosa* (45). Tobramycin-cyclam conjugates 1-3 may be interacting with a plethora of other cellular processes downstream to potentiate the effects of β-lactam antibiotics, including OM permeabilization, and perhaps against β-lactamase enzymes. Carbapenemases which belong to class A, B, and D represent the most versatile family of β-lactamases and they have the ability to hydrolyze penicillins, cephalosporins, monobactams, and carbapenems (62).

The involvement of RND efflux pumps in the synergistic interactions of compound 2 and β-lactam antibiotics appear unlikely because of the ability of compound 2 to potentiate these antibiotics (aztreonam, ceftazidime, piperacillin, meropenem, doripenem, and cefotaxime) in both WT and efflux-deficient mutant strains of *P. aeruginosa* (Table 4), as discussed below. However, it should be noted that WT PAO1 expresses efflux pumps constitutively and was still susceptible to the antipseudomonal β-lactam antibiotics studied, suggesting that resistance to β-lactam antibiotics may require, amongst other things, the over-expression of MexAB efflux pumps. Agents that alter transmembrane protein environment (such as membrane charge, fluidity, and thickness) and/or steric hindrance of membrane-embedded proteins can prevent the relay of signaling cascades required to elicit conformational changes necessary to extrude substrate molecules by efflux pumps.[13,63] The perturbation of transmembrane efflux protein domains by compound 2 via alteration of lipid composition surrounding the protein may, therefore, contribute to its ability to potentiate β-lactam antibiotics (alone and in combination with β-lactamase inhibitors) in MDR phenotypes by reducing/preventing their extrusion from the periplasmic space.

Figure 7:
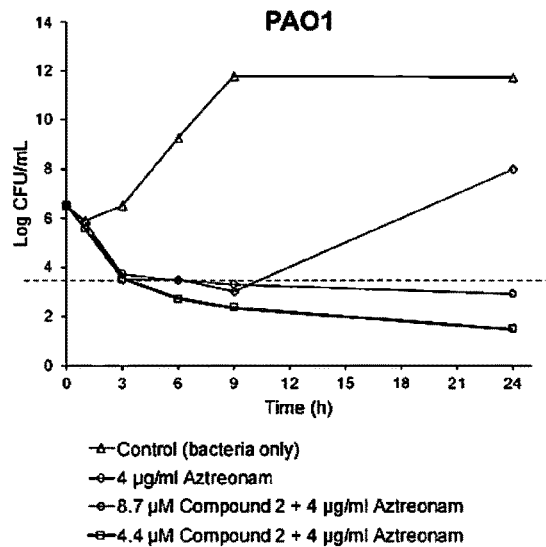
FIG. 7. Time-kill kinetics of aztreonam and meropenem, alone and in combination with different concentrations of compound 2 on the viability of; a) wild type *P. aeruginosa* PAO1, b) multidrug resistant *P. aeruginosa* 101885. MICs of aztreonam and meropenem against WT PAO1 are 4 μg/mL and 1 μg/mL, respectively. CLSI susceptibility breakpoint of aztreonam and meropenem against *P. aeruginosa* are 8 μg/mL and 2 μg/mL, respectively. Dashed line stands for a 3-Log reduction in total CFU/mL from original inoculum. Each data point is an average of three independent determinations.
Figure 7:
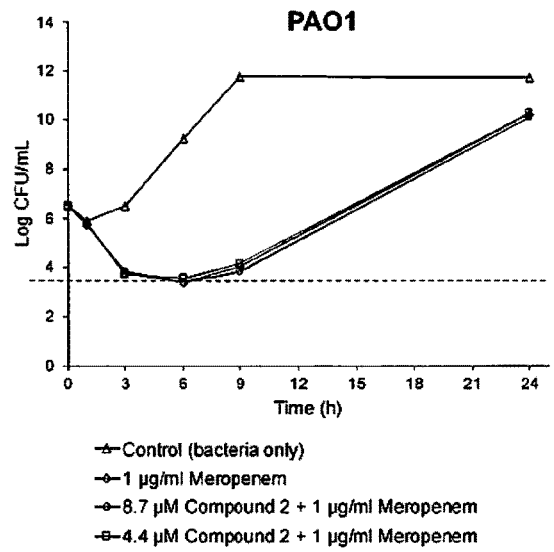
Figure 7:
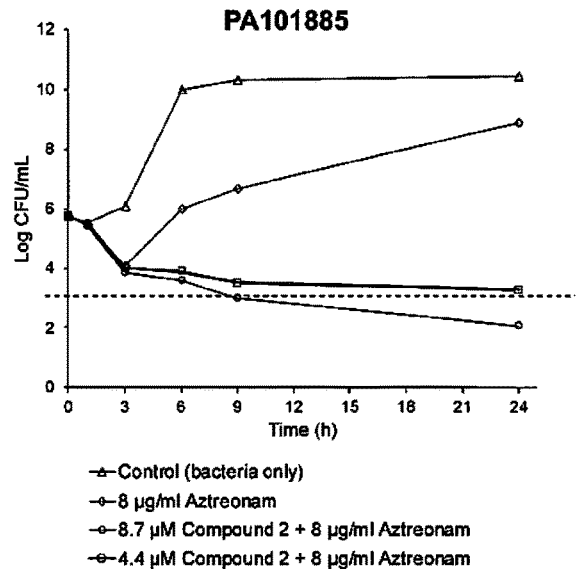
Figure 7:
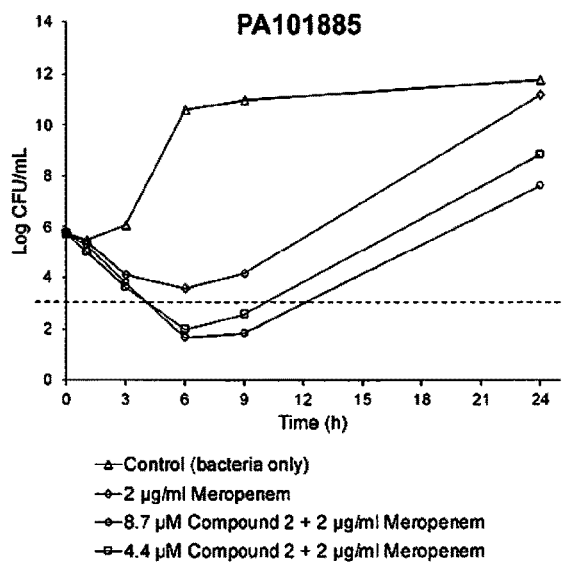

*P. aeruginosa* is often regarded as a highly challenging model organism for new antibiotics. Interestingly, the results of our study revealed that potentiation of aztreonam and meropenem was more pronounced in this organism than in other Gram-negative bacteria. Although differences in the exo- and lipopolysaccharides of *P. aeruginosa*, relative to other Gram-negative bacteria, can be hypothesized as the possible reason for this phenomenon, the best potentiation of meropenem (64-fold) by compound 2 was achieved in a colistin-resistant clinical isolate PA91433 (MIC of colistin=4 µg/mL) (FIG. 3), as discussed below. Similarly, CLSI susceptibility breakpoints were reached for aztreonam and meropenem in another highly colistin-resistant clinical isolate PA101243 (MIC of colistin=1024 µg/mL) (FIG. 5), as discussed below. A major mechanism of resistance to colistin involves modification to the lipid A component of LPS such that cationic molecules are electrostatically repelled (6). Thus, the synergistic relationships between compound 2 and meropenem or aztreonam was preserved in both colistin-susceptible and colistin-resistant phenotypes, suggesting that the action of compound 2 is independent of modifications on lipid A. β-Lactam antibiotics are bactericidal agents and the time-kill kinetics shown in FIG. 7 is congruent with this effect. The observed synergistic relationships seen between aztreonam or meropenem and compound 2 is dependent on the MIC of the antibiotic. A combination of aztreonam and compound 2 significantly reduced the bacterial counts of WT and MDR $P.$ $aeruginosa$ phenotypes in a dose- and time-dependent manner, while a combination of meropenem and compound 2 was dose-dependently synergistic against MDR PA101885 but indifferent against WT phenotype at MIC levels. These synergistic relationships are reminiscent of the synergy between meropenem and colistin (64). OM permeabilization by colistin is believed to facilitate greater concentrations of β-lactam antibiotics to reach the PBPs, thereby overcoming hydrolysis by inactivating enzymes (64). This mechanism is consistent with the observed potentiation of aztreonam or meropenem by compound 2. The regrowth observed in the combination regimen of meropenem and compound 2 (FIG. 7) is perhaps due to the selection of subpopulations resistant to meropenem at 1-2 µg/mL (65), and/or through adaptive responses to compound 2 where environmental stimuli could initiate changes in the lipid membrane. It could also be as a result of stability of both drugs in LB media at 37° C. over a 24 h period. In this study, bactericidal effects of meropenem and compound 2 were evaluated at 1-2 µg/mL and 8-16 µg/mL (i.e. 4.4-8.7 µM), respectively. However, a plasma concentration of >8 µg/mL of meropenem is achievable in humans (66), while corresponding adjuvants are usually evaluated in vitro at concentrations >20 µM (31, 66).

The use of definitive combination therapy including two (or more) antibiotics to which a bacteria strain is susceptible has been suggested to improve bacteriological clinical outcome when compared with monotherapy, especially for $P.$ $aeruginosa$ infections (67), but clinical data to support the choice of antibiotic combinations are sparse and conflicting, and meta-analyses of these treatment regimens are often contradictory (68, 69), except for tuberculosis (13). However, the use of β-lactam antibiotics and β-lactamase inhibitors (non-antibiotics) has been very successful (24), as evident in the successes of legacy combinations of amoxicillin-clavulanic acid, ampicillin-sulbactam, piperacillin-tazobactam, and more recently, ceftazidime-avibactam, meropenem-vaborbactam, and ceftolozane-tazobactam combinations. At least four more β-lactam-based antibiotic-adjuvant combinations are currently in clinical trials (70, 71). Unfortunately, resistance to these combinations are rapidly emerging (24). β-Lactamases are typically found in the periplasmic space of Gram-negative bacteria, and the rapidity with which inhibitors can access their targets is critical for successful inhibition (24). We show that the addition of a second non-antibiotic component that can permeabilize the OM can further potentiate the effects of β-lactam/β-lactamase inhibitor combinations against recalcitrant pathogens (FIG. 6), as discussed below. Avibactam alone, a β-lactamase inhibitor, reverses the resistance of β-lactamase-harboring MDR $P.$ $aeruginosa$ phenotypes to ceftazidime, aztreonam, and meropenem at high concentrations (FIG. 6), but in the presence of 8 µM of compound 2, the effect of avibactam+β-lactam antibiotics was significantly potentiated (FIG. 6), as discussed below. Time-kill kinetics further revealed a synergistic pharmacodynamic interaction between ceftazidime/avibactam and compound 2 against β-lactamase-harboring MDR PA108590 within 3 h of incubation (FIG. 8), as discussed below. These findings underscore the sophisticated complementary mechanisms of resistance in $P.$ $aeruginosa$, and that β-lactam/β-lactamase inhibitor combinations can be greatly improved by adding a second OM permeabilizing adjuvant. On the contrary, compound 2 did not improve the therapeutic efficacy of ceftolozane-tazobactam combination, the most potent cephalosporin against $P.$ $aeruginosa$ (72), perhaps due to the fact that the isolates were innately susceptible to this combination. Ceftolozane appears to be unaffected by the multitude of resistance mechanisms employed by $P.$ $aeruginosa$, including overexpression of AmpC, reduced porin uptake, efflux, and modification of PBPs (72, 73).

In vivo studies using $G.$ $mellonella$ infection model show that in vitro synergism of β-lactam/compound 2 and β-lactam/β-lactamase inhibitor/compound 2 were translated in vivo. The larvae tolerated up to 200 mg/kg each of aztreonam, meropenem, ceftazidimen, and compound 2 (FIG. 9a). Efficacy studies (3 h post infection with MDR PA101885) showed that monotherapy of aztrconam (12.5 mg/kg), meropenem (37.5 mg/kg), or compound 2 (100 mg/kg) resulted in 100% mortality of the larvae after 24 h (FIG. 9b). However, a single dose combination therapy of aztrconam+compound 2 (12.5+12.5 mg/kg) and meropenem+compound 2 (37.5+37.5 mg/kg) resulted in 100% and 85% survival, respectively, after 24 h (FIG. 9b). Furthermore, ceftazidime alone (1.56 mg/kg) and ceftazidime+avibactam (1.56+1.56 mg/kg) resulted in 50% and 70% survival of PA108590-challenged worms after 24 h while ceftazidime+avibactam+compound 2 resulted in 100% survival after 24 h (FIG. 9c). The ability of these combinations to offer protection to MDR $P.$ $aeruginosa$-challenged larvae in a dose-dependent manner confirms their therapeutic potentials. Compounds 1-3 were non-cytotoxic to human kidney (HEK293) and liver (HepG2) cells in vitro (FIG. 10a), non-hemolytic to porcine erythrocytes in vitro (FIG. 10b), and non-toxic to $G.$ $mellonella$ larvae in vivo (FIG.

9a). This rules out a non-specific membranolytic mode of action and indicates the relative safety of these compounds towards eukaryotic cells.

According to an aspect of the invention, there is provided a compound comprising a chemical structure or chemical formula of Formula (A):

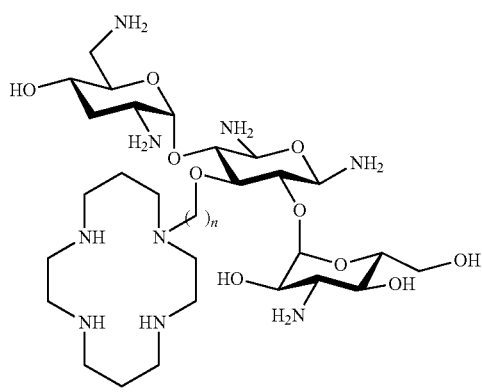

(A)

or a suitable salt form thereof, wherein "n" is a carbon tether having a length of between about 2-18 carbons.

As discussed herein, "carbon tether" does not mean that the tether must be composed of only carbon atoms, but rather a tether that has a length similar or approximate to that of 2-18 carbons. For example, the carbon tether could contain polyethyleneglycol units (O—CH2-CH2)n (n=1-10).

According to another aspect of the invention, there is provided a compound comprising a chemical structure or chemical formula of formula (I)

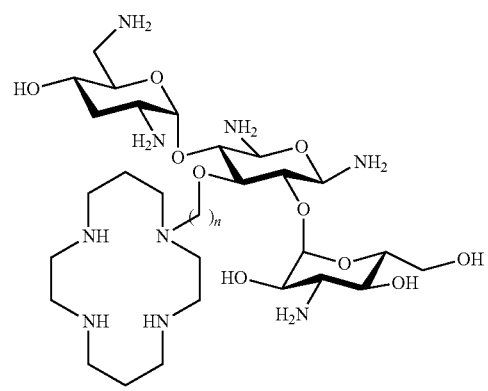

(I)

1: n = 4 (X 9TFA)
2: n = 8 (X 9TFA)
3: n = 12 (X 9HCl)

or a suitable salt form thereof.

According to an aspect of the invention, there is provided a compound consisting of a chemical structure or chemical formula of formula (I)

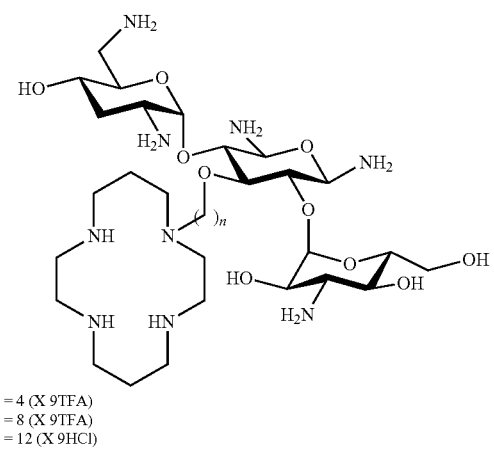

(I)

1: n = 4 (X 9TFA)
2: n = 8 (X 9TFA)
3: n = 12 (X 9HCl)

or a suitable salt form thereof.

It is to be understood that while the above formulae refer to trifluoroacetic acid (TFA) salts with respect to compounds with n=4 or n=8 as the tether and hydrochloric acid (HCl) salt with respect to n=12 as the tether, the formula (I) is intended to represent both neutral and suitable salt forms of the compound. It should further be noted that TFA and HCl represent two exemplary examples of suitable salts, others of which will be readily apparent to one of skill in the art.

In some embodiments, the compound is an antibiotic adjuvant.

According to another aspect of the invention, there is provided a method of perturbing or permeabilizing or destabilizing or increasing the fluidity of the outer membrane of a gram-negative bacterium comprising: administering to an individual in need of such treatment an effective amount of compound comprising a chemical structure of Formula (I) or a salt thereof, as set forth above.

In some embodiments, the gram-negative bacterium is for example but by no means limited to a *Pseudomonas*, for example, a *Pseudomonas aeruginosa, Acetinobacter baumannii, E. coli, Klebsiella pneumoniae*, Enterobacteriaceae and other bacteria.

According to another aspect of the invention, there is provided use of a compound for perturbing or permeabilizing or destabilizing or increase the fluidity of the outer membrane of a gram-negative bacterium, said compound comprising the chemical structure of Formula (I), as set forth above.

An individual in need of such treatment is an individual who has, is known to have, has been diagnosed as having or is suspected of having a bacterial infection caused by a gram-negative bacterium.

In some embodiments, the gram-negative bacterium may be a multi-drug resistant bacterium (MDR), an XDR or a PDR.

In some embodiments, the gram-negative bacterium is a *Pseudomonas*.

In some embodiments, the compound is co-administered with an effective amount of an antibiotic.

As will be appreciated by one of skill in the art, as used herein, "co-administered" does not require that the adjuvant compound and the antibiotic be administered at exactly the same time but that they be administered within a time frame during which both the adjuvant compound and the antibiotic are biologically active or effective.

As will be appreciated by one of skill in the art, an "effective amount" of the compound, that is, that is sufficient to increase the fluidity of the outer membrane of a gram-negative bacterium, may be determined for example by measuring the change in fluidity resulting from different concentrations. Alternatively, the effective amount may be determined functionally, for example, by determining the amount that is sufficient so that the rate of antibiotic influx surpasses the rate of active antibiotic export.

In some embodiments, "an effective amount" may be 1-200 µM or 0.5-113 mg/L of the compound.

As will be appreciated by one of skill in the art, any suitable antibiotic may be used within the invention, for example, antibiotics from various antibiotic classes including but not limited to β-lactam antibiotics, β-lactam inhibitors and combinations thereof.

The β-lactam antibiotic may be for example but by no means limited to a monobactam, a penicillin, a cephalosporin or a carbapenem.

The cephalosporin may be for example but by no means limited to cefaclor; cefoxitin; cefoteton; cefamandole; cefmetazole; cefonicid; loracarbef; cefprozil; cefuroxime; cefixime; cefdinir; cefoperazone; cefotaxime; cefpodoxime; ceftazidime; ceftibuten; ceftozoxime; latamoxef; ceftriaxone; cefepime; ceftobiprole, ceftolozane or combinations thereof.

The monobactam may be for example aztreonam.

The penicillin may be for example amoxicillin, flucloxacillin or piperacillin.

The penicillin may be a combination and may be for example amoxixillin/clavulanate; ampicillin/sulbactam; piperacillin/tazobactam; or ticarcillin/clavulanate.

The carbapenem may be meropenem, doripenem, imipenem, ertapenem, panipenem, biapenem, or tebipencm The ☐-lactam inhibitor may be for example but by no means limited to clavulanic acid, sulbactam, tazobactam, avibactam, relebactam, or vaborbactam.

The invention will now be further elucidated and explained by way of examples; however, the invention is not necessarily limited by or to the examples.

Results

Example 1—Design and Synthesis

Figure 11:
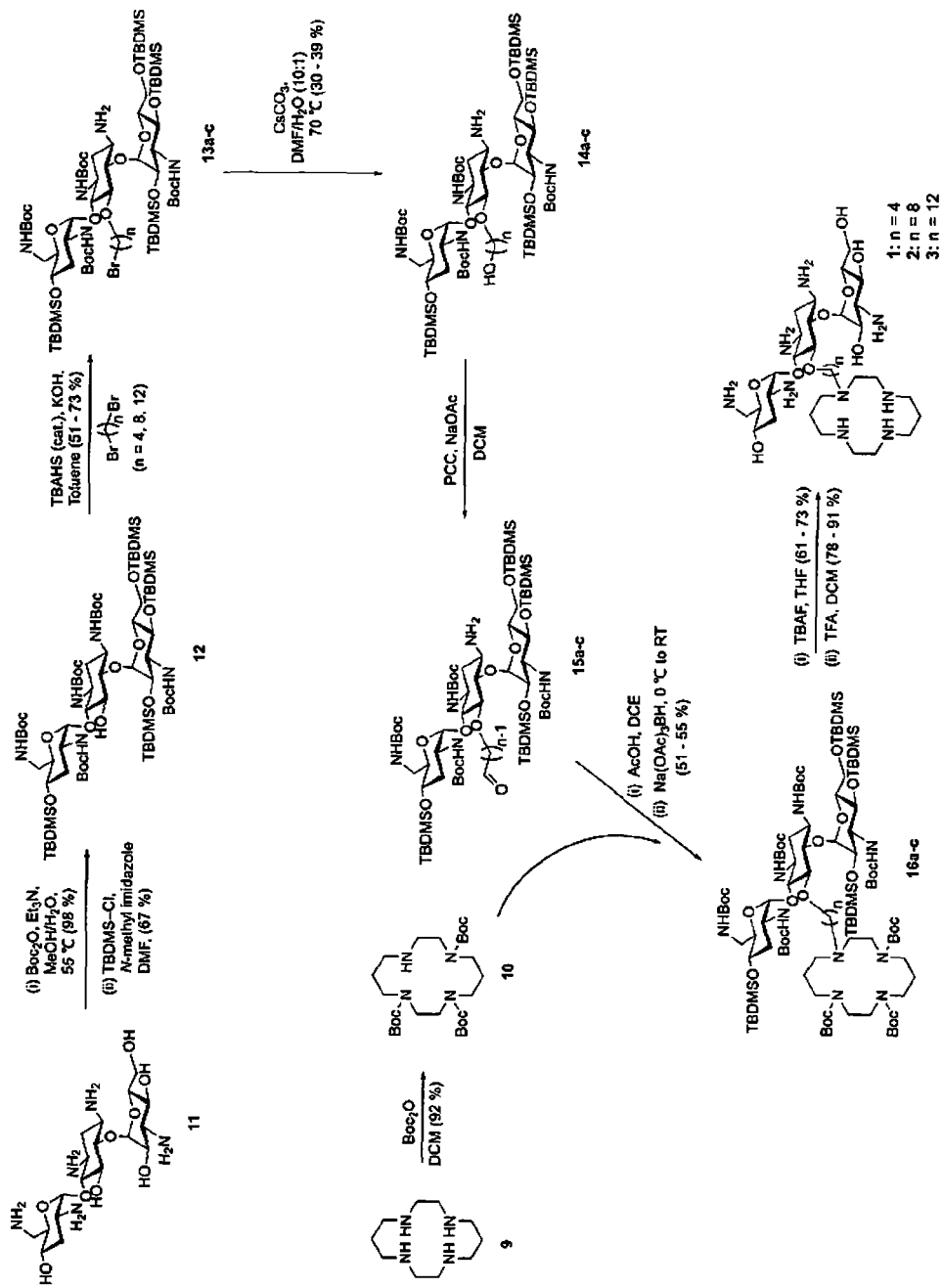
FIG. 11. Synthesis of Tobramycin-Cyclam conjugates 1-3.

The design of tobramycin-cyclam conjugates (FIG. 1) was established from previous structure-activity relationships. Amphiphilic tobramycins with lipophilic groups at the C-5 position have been shown to lose ribosomal activities but retain the ability to permeabilize the OM of P. aeruginosa (13, 20). A lipophilic cationic neamine grafted to a cyclam moiety, a chelating agent, has also been reported to permeabilize the OM of E. aerogenes (34). Thus, tobramycin and cyclam were conjoined to each other at the C-5 position of tobramycin, using aliphatic hydrocarbon of different tether lengths, i.e. C-4, C-8, and C-12. The use of aliphatic hydrocarbon linker was to preserve the amphiphilic nature of amphiphilic tobramycins, while the various tether length was meant to investigate the optimal spatial separation between the two domains. Ligation of the resulting amphiphilic tobramycin to a cyclam domain was achieved via reductive amination in order to preserve the cationic nature of all the secondary amines of cyclam. The final compounds were prepared as TFA and HCl salts in order to investigate the effect of different salt forms on biological activities. The synthetic strategy for preparing compounds 1-3 is outlined in Scheme 1 (FIG. 11).

Example 2—Chemical Synthesis of Tobramycin-Cyclam Conjugates 1-3

The amphiphilic tobramycin domain was prepared following previously reported protocol (35). Tobramycin 11 was purchased from a commercial source and the amino groups were first protected using di-tert-butyl dicarbonate (Boc anhydride), followed by silylation of the N-Boc-tobramycin intermediate with excess TBDMSCl to afford a partially protected derivative 12 with free OH at the C-5 position of the cyclitol ring. Alkylation of 12 in toluene with 1,n-dibromoalkane (n=4, 8, 12) in the presence of a phase-transfer catalyst (TBAHS) afforded bromoalkylated TBDMS-Boc-protected tobramycin intermediates. The terminal bromo-groups of these intermediates were then hydrolysed to afford compounds 14a-c and subsequently oxidized to their corresponding aldehydes 15a-c using PCC. Compounds 16a-c were prepared via reductive amination of aldehydes 15a-c with (Boc)$_3$-protected cyclam 10, followed by stepwise deblocking—first by removing TBDMS groups using TBAF, then removing the Boc-protecting groups using TFA—to afford the final compounds 1-3 (FIG. 11).

Example 3—Antimicrobial Susceptibility Screening

The antimicrobial activities of compounds 1-3 were assessed against a panel of Gram-positive and Gram-negative bacteria, and compared to the parent molecule, tobramycin, as shown in table 1. Whereas tobramycin by itself exhibited low MIC values (≤2 µg/ml) against susceptible strains, indicating potency, the MICs of conjugates 1-3 (≥16 µg/ml) were significantly greater than tobramycin against all strains, indicating a significant loss of activity. Compounds 1-3 were also inactive against Gram-positive bacteria which do not have an OM permeability barrier. This result is consistent with our hypothesis that a C-5 conjugation will abolish the ribosomal effects of tobramycin. The antipseudomonal activities of compounds 1-3 and tobramycin were further evaluated against a panel of MDR/XDR P. aeruginosa clinical isolates obtained from CANWARD (36, 37) and intensive care units (38) of different Canadian hospitals. These clinical isolates were either intermediately or completely resistant to carbapenems, and some were also resistant to colistin. As expected, compounds 1-3 displayed poor activity against these organisms as standalone antibacterial agents (MIC>256 µg/ml). The tether length between the tobramycin and cyclam domains does not play any significant role in the antimicrobial properties of these compounds as standalone antimicrobial agents.

Example 4—Combination Studies of Tobramycin-Cyclam Conjugates with Different Classes of Antibiotics Against Wild-Type P. aeruginosa The apparent lack of antibacterial activity of the newly synthesized compounds further encouraged us to investigate their adjuvant properties. An ideal adjuvant is a bioactive helper molecule that does not possess antibacterial activity by itself but can potentiate the effect of a primary antibiotic and/or delay resistance development when used in combination (13, 39). This type of compound is less likely to select for resistance (39). To investigate this effect, checkerboard studies were used to assess the interactions between compounds 1-3 and twenty-three different antibiotics (representing all major classes of antibiotics) against wild-type *P. aeruginosa* PAO1 (Table 2). *P. aeruginosa* was selected because OM permeability is a major mechanism by which it evades antibiotic activity. Data from this study were interpreted as a function of the fractional inhibitory concentration index (FICI), a numerical quantification of the interactions between antimicrobial agents. FICI of <0.5, 0.5-4, and >4 indicate synergy, additive or no interaction, and antagonism, respectively.[13,20] Results of this study show that at a low concentration of ≤10 μM (≤16 μg/mL), i.e. ⅟₆₄×MIC, compounds 1-3 strongly potentiate the effects of different classes of antibiotics against WT *P. aeruginosa* PAO1, including β-lactams (FICI=0.007-0.25), rifampicin (FICI=0.13-0.25), novobiocin (FICI=0.08-0.13), tetracyclines (FICI=0.08-0.25), etc., but not tobramycin (FICI=1), nitrofurantoin (FICI=1), and colistin (FICI=2) (Table 2, FIG. 2a). *P. aeruginosa* PAO1 is a wild-type phenotype that is susceptible to all antipseudomonal agents used in the study, hence, the ability to potentiate antipseudomonal agents (especially β-lactams) against this strain suggests a mechanism that is independent of acquired resistance mechanisms. These synergistic effects were generally dose-dependent and the highest adjuvant concentration of 10 μM (i.e. 16 μg/mL) used to evaluate synergistic relationships is a clinically-achievable therapeutic concentration of aminoglycosides (20-200 μM, i.e. 10-113 mg/L) in human plasma.[40,41] None of the combinations had an antagonistic relationship. The lack of complementary synergism between compounds 1-3 and colistin (Table 2, FIG. 2a) further corroborates the postulation that the loss of potent standalone activity of conjugates 1-3 is not due to the inability to cross the OM, but likely due to the abrogation of their ribosomal effects. Colistin is a well-known OM permeabilizer that potentiates OM-impermeable antibiotics against Gram-negative bacteria (42). Unlike in susceptibility testing, the tether length of compounds 1-3 plays a role in the degree of potentiation but not the type of antibiotic potentiated. For instance, compounds 1-3 potentiated almost the same antibiotics against WT PAO1 (FIG. 2a) but the fold reduction in MICs varied from one compound to the other (FIG. 2b). The ability to reproducibly potentiate β-lactam antibiotics was quite remarkable as these drugs traverse the OM of *P. aeruginosa* via porin (OprD and OprF) channels, although decreased expressions of these OM proteins have been associated with resistance to β-lactam antibiotics in *P. aeruginosa* (26, 43). Compound 2 was the best potentiator of aztreonam and ceftazidime against WT PAO1, and exhibit physicochemical properties with the least propensity for toxicity (hydrophobic-charge ratio) and non-specific protein binding, hence, it was selected for further studies with (3-lactam antibiotics against carbapenem-resistant isolates.

Figure 3:
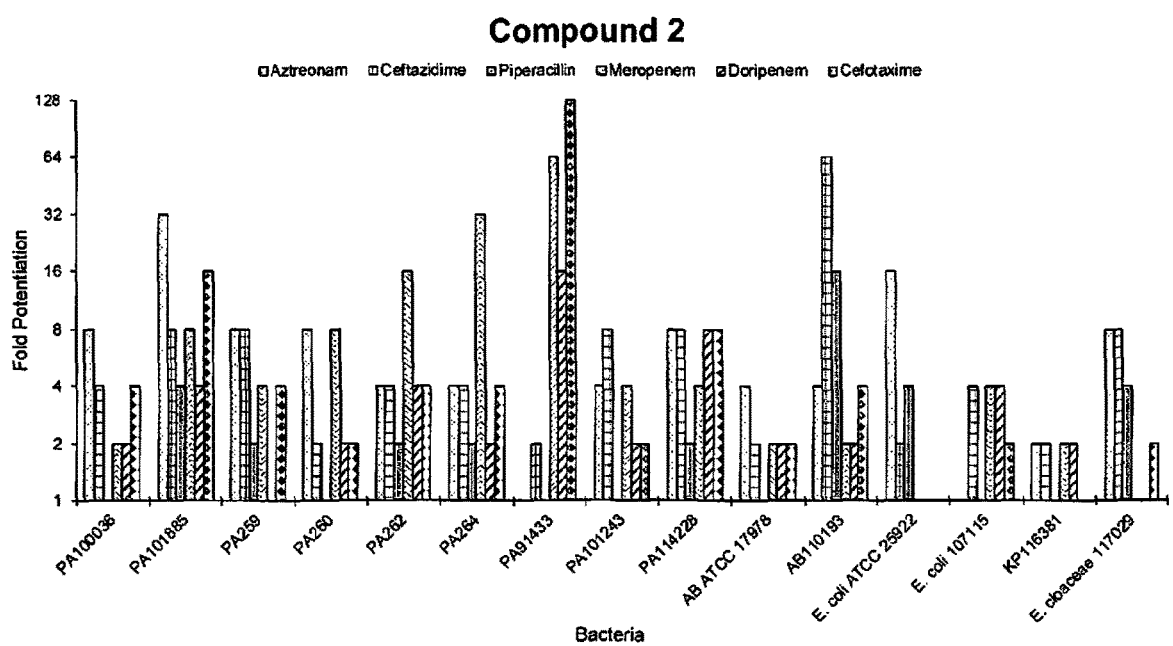
FIG. 3. Fold change in susceptibility of resistant clinical isolates of *P. aeruginosa* (PA) to select β-lactam antibiotics in the presence of 8.7 μM of compound 2.
Figure 4:
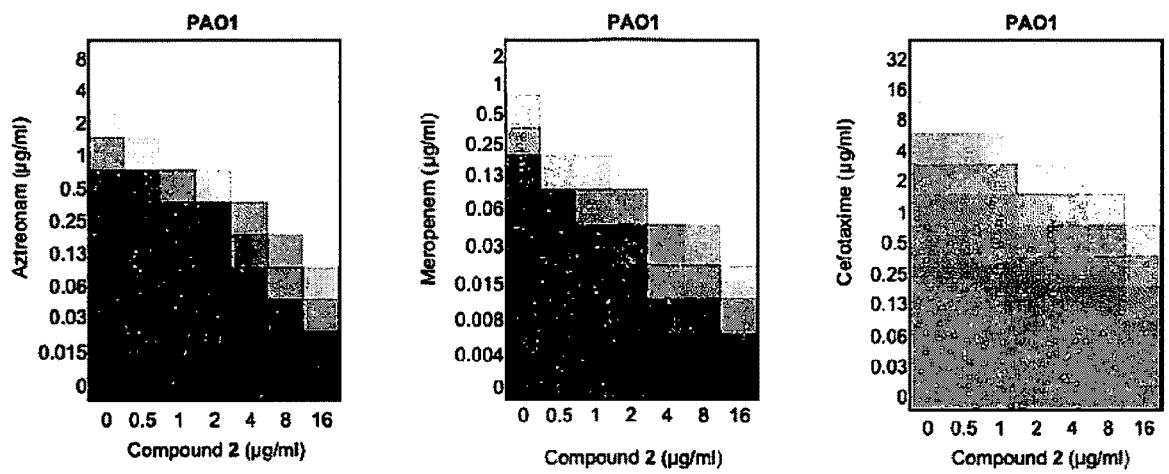
FIG. 4. Compound 2 overcomes resistance to β-lactam antibiotics in *P. aeruginosa*. Representative checkerboard broth microdilution assays showing dose-dependent potentiation of aztreonam, meropenem, and cefotaxime against (a) wild-type *P. aeruginosa*, (b) MDR/XDR/PDR *P. aeruginosa* clinical isolates obtained from wards and intensive care units of different Canadian hospitals. Dark colours represent higher cell density (OD measured at 590 nm). 16 μg/ml of compound 2=8.7 μM.
Figure 4:
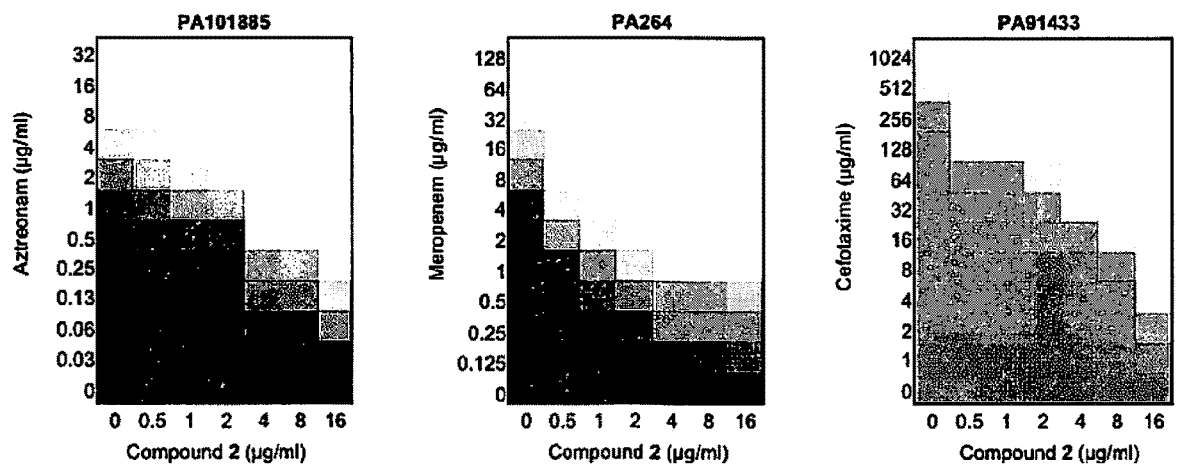
Figure 5:
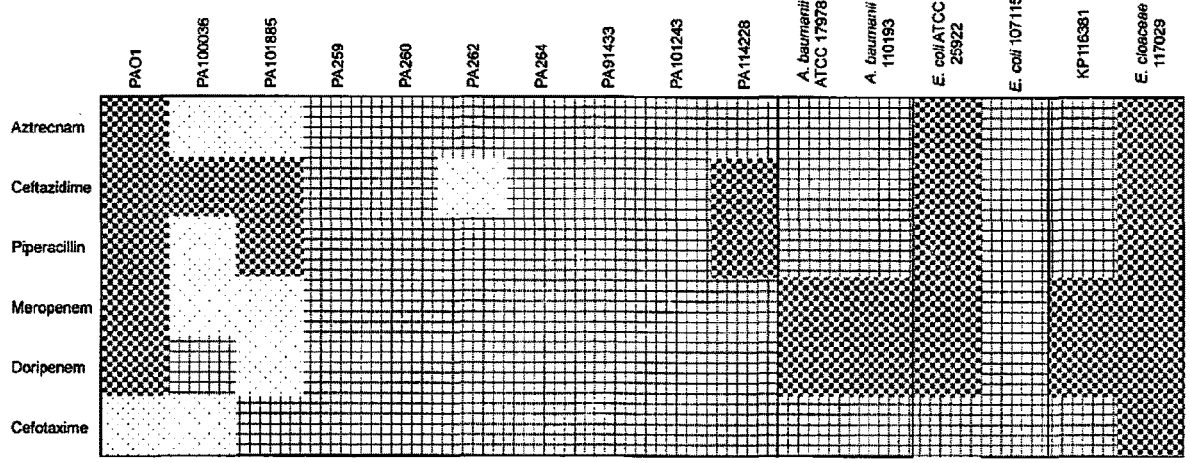
FIG. 5. CLSI susceptibility profiles of wild-type, multidrug-resistant, and extensively drug-resistant Gram-negative bacteria when treated with select β-lactam antibiotics a) alone, b) in combination with 8.7 μM of compound 2. PA=*Pseudomonas aeruginosa*, KP=*Klebsiella pneumoniae*.
Figure 5:
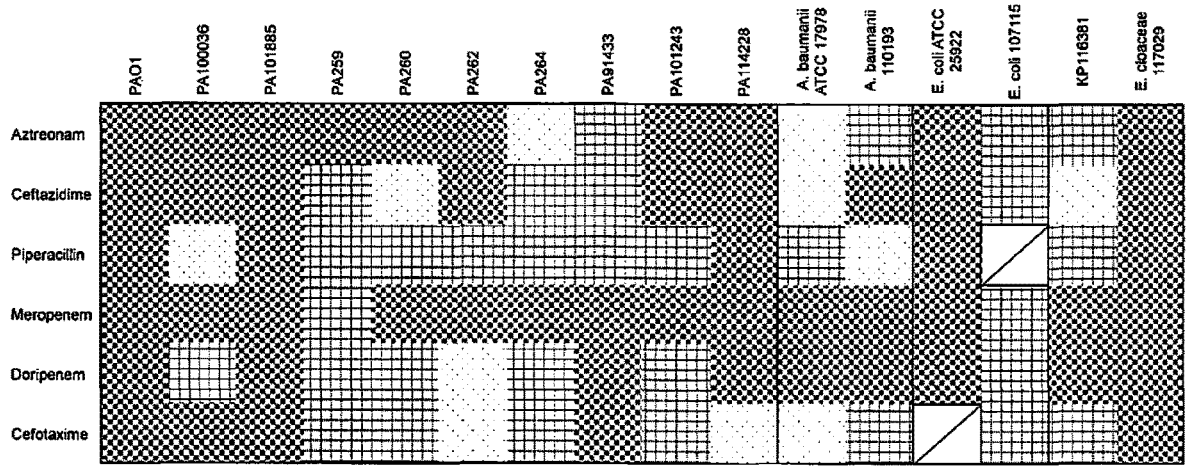
Figure 5:

Example 5—Tobramycin-Cyclam Conjugate Potentiates the Activities of pβ-Lactam Antibiotics Against Resistant *P. aeruginosa* Clinical Isolates To investigate whether potentiation of β-lactam antibiotics is conserved beyond WT PAO1, we assessed the synergistic relationships between compound 2 and six β-lactam antibiotics against nine MDR/XDR *P. aeruginosa* phenotypes. These antibiotics include one penicillin (piperacillin), one monobactam (aztreonam), two cephalosporins (ceftazidime and cefotaxime), and two carbapenems (meropenem and doripenem). The isolates screened were all resistant to all the β-lactams tested. Encouragingly, compound 2 (at ≤8.7 μM) retained the ability to potentiate all six antibiotics against the various *P. aeruginosa* clinical isolates (Table 3). For example, susceptibility to aztreonam was increased by 4- to 32-fold in eight out of nine strains, ceftazidime was increased by 4- to 8-fold in seven out of nine strains, piperacillin was increased by 4-fold in one out of nine strains, meropenem was increased by 4- to 64-fold in eight out of nine strains, doripenem was increased by 4- to 16-fold in four out of nine strains, and cefotaxime was increased by 4- to 128-fold in seven out of nine strains (FIG. 3). Similar to WT PAO1, the synergistic effects of compound 2 and its degree of potentiation were also dose-dependent against most of the clinical isolates studied (FIG. 4). Importantly, susceptibilities equal to or below CLSI clinical breakpoints were achieved for: aztreonam (≤8 μg/ml) in seven out of nine resistant isolates, ceftazidime (≤8 μg/ml) in three out of six resistant isolates, piperacillin (≤16 μg/ml) in zero out of six resistant isolates, meropenem (≤2 μg/ml) in eight out of nine resistant isolates, doripenem (≤2 μg/ml) in three out of nine resistant isolates, and cefotaxime (≤8 μg/ml) in four out of ten resistant isolates (FIG. 5). *P. aeruginosa* is intrinsically resistant to cefotaxime, hence, the CLSI breakpoint for *Acinetobacter* spp. was used as interpretive reference (44). Overall, nine out of nine MDR/XDR *Pseudomonas* phenotypes demonstrate the attainment of therapeutic levels of susceptibilities to at least one of the six β-lactam/compound 2 combinations, with aztreonam and meropenem showing the best therapeutic potential in seven out of nine and eight out of nine, respectively (FIG. 5). In contrast, CLSI susceptibility breakpoints could not be reached for any of the β-lactam/compound 2 combination tested against other Gram-negative bacteria resistant isolates, except for ceftazidime/compound 2 combination against *A. baumannii* 110193 (FIG. 5). It is noteworthy that aztreonam and meropenem were more potentiated in *P. aeruginosa* than in other Gram-negative bacteria while piperacillin and ceftazidime were more potentiated in MDR *A. baumannii* than in *P. aeruginosa* (FIG. 3).

Example 6—Tobramycin Alone, Cyclam Alone, or a Combination of Both does not Potentiate Aztreonam and Meropenem Against *P. aeruginosa*

To probe if tobramycin alone or cyclam alone could potentiate the effects of β-lactam antibiotics against *P. aeruginosa*, we investigated their interactions with aztreonam and meropenem against WT, tobramycin-susceptible MDR, and tobramycin-resistant XDR phenotypes. Aztreonam and meropenem were selected because they showed the best potentiation effects with compound 2 against all *P. aeruginosa* isolates tested. Our results show that tobramycin by itself could neither potentiate aztreonam nor meropenem against WT (FICI=0.75-1.00), tobramycin-susceptible MDR (FICI=0.75), and tobramycin-resistant MDR/XDR isolates (FICI=0.56-0.75). At best, tobramycin only increased the susceptibility of tobramycin-resistant MDR/XDR strains to aztreonam and meropenem by 4- to 8-fold at one-half its MIC levels (up to 256 μg/ml), a concentration that is relatively toxic and clinically unachievable in human plasma (40). Also, none of the combinations had an antagonistic effect. These observations are consistent with the reported ability of meropenem to potentiate some aminoglycosides, but not tobramycin, against *P. aeruginosa* (45). Similarly, there was no synergistic relationship between cyclam (FICI=2.00) and any of aztreonam, ceftazidime, piperacillin, meropenem, doripenem, and cefotaxime against WT *P. aeruginosa* PAO1.

Example 7—Potentiation of β-Lactam Antibiotics is Independent of RND Efflux Pumps To ascertain whether tobramycin-cyclam conjugate 2 interferes with efflux mechanisms in increasing the susceptibility of WT PAO1 to β-lactam antibiotics, two mutant strains, PAO200 and PAO750, lacking different clinically-relevant efflux pumps were assessed for potentiation of aztreonam, ceftazidime, piperacillin, meropenem, doripenem, and cefotaxime by conjugate 2. PAO200 is a mexA-mexB-oprM deletion strain while PAO750 lacks five important RND pumps (McxAB-OprM, MexCD-OprJ, MexEF-OprN, Mex JK, and MexXY) and the outer membrane protein OpmH (46, 47). Some of these pumps are homologues of broad substrate specificities that extrude different classes of antimicrobial agents and confer resistance on *P. aeruginosa* (48). As expected, PAO200 showed increased susceptibility to all β-lactam antibiotics tested except doripenem (Table 4), consistent with known contributions of MexAB-OprM pumps to intrinsic Ji-lactam resistance (49). Similarly, PAO750 exhibited increased susceptibility to aztreonam, ceftazidime, and piperacillin, equal susceptibility as WT PAO1 to meropenem and doripenem, and a two-fold reduced susceptibility to cefotaxime (Table 4). There was no notable change in the susceptibility of WT and efflux-deficient *P. aeruginosa* mutants to conjugates 1-3, suggesting that tobramycin-cyclam conjugates are not substrates for the RND efflux pumps. This also confirms that the lack of intrinsic activity of these conjugates is not because of their active efflux from the cell, although AGs are known to be actively extruded by some of these RND efflux pumps (48, 49). Interestingly, the ability of compound 2 to potentiate the activities of aztreonam, ceftazidime, meropenem, and doripenem in WT PAO1 was retained, to the same extent or more, in efflux-deficient mutant strains PAO200 and PAO750 (Table 4), an indication that potentiation in WT *P. aeruginosa* is not dependent on the presence or interactions with RND efflux pumps. Cefotaxime was exceptionally potentiated by compound 2 against PAO750 while piperacillin and cefotaxime were not potentiated against PAO200.

Example 8—Potentiation of β-Lactam/β-Lactamase Inhibitor Combinations Against β-Lactamase-Harboring *P. aeruginosa* Clinical Isolates (Triple Combination Therapy)

Figures 1, 6:
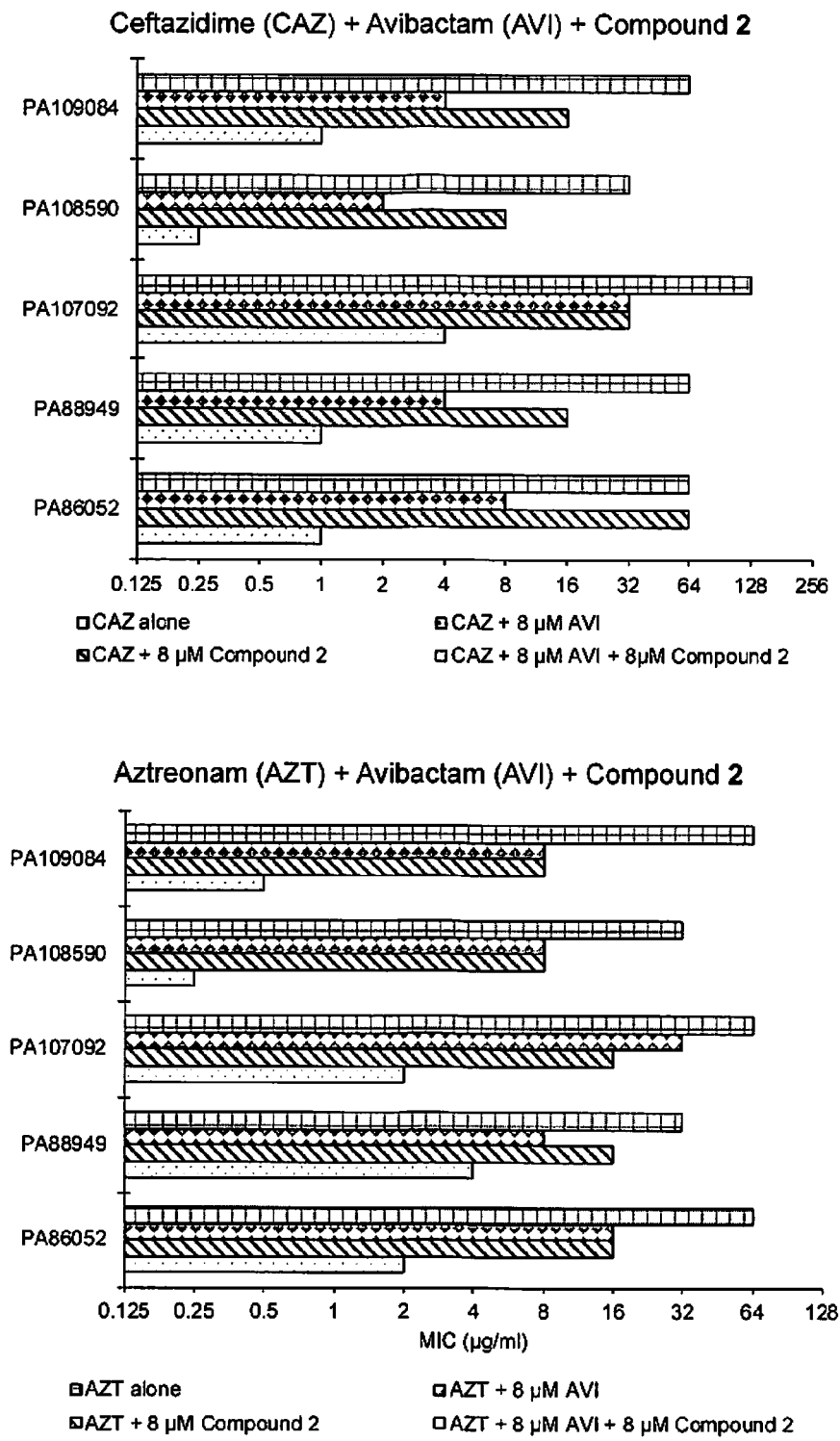
FIG. 6. Triple combination therapy versus double combination versus monotherapy against β-lactamase-harboring MDR *P. aeruginosa* isolates. CAZ=ceftazidime, AZT=aztreonam, MER=meropenem, AVI=avibactam. 8 μM avibactam≈2 μg/mL; 81 μM compound 2≈16 μg/mL.
Figures 2, 6:
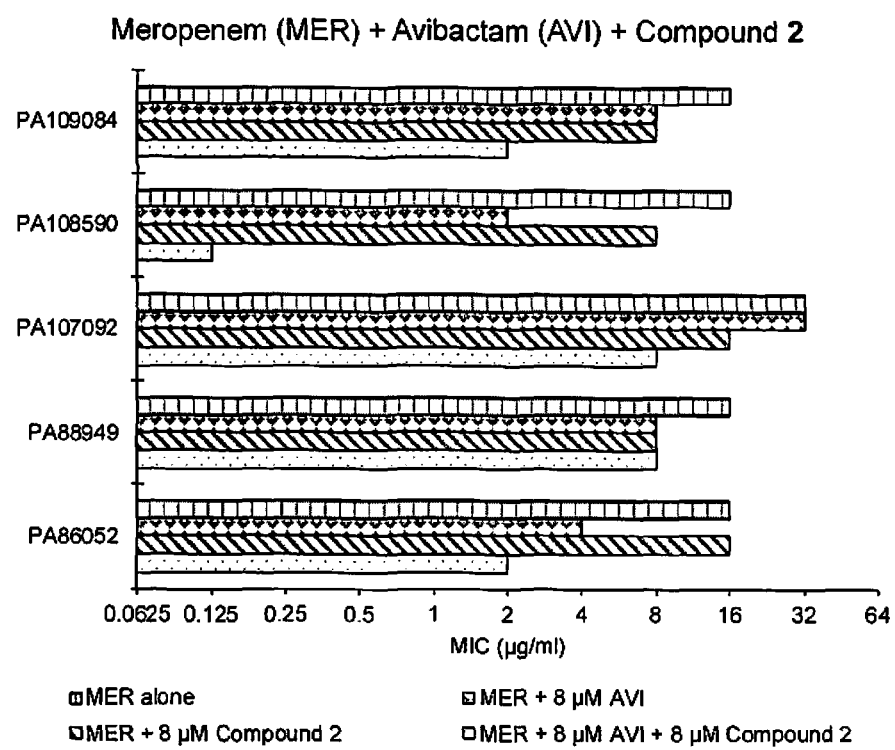

To investigate whether a triple combination of a β-lactam antibiotic+a β-lactamase inhibitor+compound 2 will be more efficacious than a double combination of a β-lactam antibiotic+a β-lactamase inhibitor or a β-lactam antibiotic+ compound 2, we evaluated the susceptibilities of five different β-lactamase-harboring MDR *P. aeruginosa* phenotypes to β-lactam antibiotics (ceftazidime, aztreonam, meropenem) in combination with fixed equimolar concentrations of avibactam and compound 2 (FIG. 6). The main mechanism of resistance of these isolates to β-lactam antibiotics was posited to be over-expression of inducible AmpC β-lactamase enzymes due to the ability of avibactam to completely reverse resistance to ceftazidime and aztreonam at 4-16 µg/ml (16-64 µM), but not meropenem. The diazabicyclooctane β-lactamase inhibitor, avibactam, is able to inhibit a wide range of serine β-lactamases (class A, C, and D) but not metallo-β-lactamases (class B) (50, 51).[50,51] However, the high concentration of avibactam required to neutralize the effects of β-lactamase enzymes in these phenotypes is indicative of concomitant permeability barriers in the isolates, such as reduced porin uptake. Thus, we combined 8 µM of avibactam (~2 ng/ml) with 8 µM of compound 2 (~16 µg/ml) and investigated their effects on the susceptibilities of the β-lactamase-harboring isolates to ceftazidime, aztreonam, and meropenem. The results of this study are shown in (FIG. 6). All isolates were resistant to all three β-lactam antibiotics used for the study. Avibactam, at 8 µM (2 µg/ml), potentiated the effect of ceftazidime by 4- to 16-fold and reached susceptibility breakpoint of ≤8 µg/ml in four out of five isolates, while compound 2, at 8 µM (16 µg/ml), potentiated ceftazidime by 4-fold and reached susceptibility breakpoint in one of five isolates. However, a combination of 8 µM each of avibactam and compound 2 potentiated ceftazidime by 32- to 128-fold and achieved susceptibility levels far below susceptible breakpoints in all isolates (FIG. 6). For aztreonam, avibactam (8 µM) or compound 2 (8 µM) potentiated its effect by 2- to 8-fold and susceptibility breakpoint of ≤8 µg/ml was reached in three out of five and two out of five isolates, respectively, while a combination of avibactam and compound 2 (8 µM each) potentiated aztreonam by 8- to 128-fold and achieved susceptibilities below susceptible breakpoints in all five isolates (FIG. 6). As expected, the study with meropenem was slightly different from others. Avibactam (8 µM) or compound 2 (8 µM) potentiated meropenem by only 2- to 4-fold and reached susceptibility level in only one of five and zero of five isolates, respectively. However, a combination of avibactam and compound 2 (8 µM each) potentiated meropenem by 2- to 128-fold and reached susceptible levels in three out of five isolates (FIG. 6). These results are consistent with OM permeabilization and increased bioaccumulation of β-lactam antibiotics and β-lactamase inhibitors in the periplasmic space, hence, better activity in vitro. PA108590 isolate exhibited the highest susceptibility (128-fold potentiation) to all three β-lactam antibiotics used in triple combination with avibactam and compound 2. Compound 2 did not improve the activity of ceftolozane-tazobactam combinations against all the β-lactamase-harboring *P. aeruginosa* isolates tested.

Time-kill Assay

Time-kill curves typically reveal the kinetics of bacterial growth and death, with respect to time, at different antimicrobial concentrations. An antibiotic could either be bactericidal or bacteriostatic under specific growth conditions. Bactericidal activity is defined as a ≥3-log reduction in the total CFU/mL from the original inoculum over 24 hours while bacteriostatic activity is defined as maintenance of <3-log reduction in the total CFU/mL from the original inoculum (44). Synergy is defined as ≥2-log decrease in the number of CFU/ml between the combination and the most active component of the combination after 24 h (at least one of the drugs must be present at a concentration that does not affect the growth curve of the test organism) (52). Growth curves were initially performed to ensure that strains will reach a stable early- to mid-log phase after 4 h of pre-incubation in antimicrobial-free LB medium.

Double Combination Therapy.

The growth curves for both WT PAO1 and MDR PA101885 phenotypes typically had a lag phase of under 3 h (FIG. 7). The kinetics of killing of WT PAO1 and PA101885 MDR phenotype using monotherapy of aztreonam and meropenem, as well as their respective combinations with compound 2, were therefore assessed by time-kill assay in LB media. The results of the study revealed that aztreonam and meropenem alone exhibit a time-dependent bactericidal effect in WT PAO1 at their respective MIC levels (i.e. 4 µg/mL and 1 µg/mL respectively), but a bacteriostatic effect in MDR PA101885 at their respective CLSI breakpoint concentrations, i.e. 8 μg/mL and 2 μg/mL, respectively (FIG. 7). However, when combined with 4.4 μM or 8.7 μM of compound 2, the effects of aztreonam and meropenem became strongly bactericidal at their respective CLSI breakpoint concentrations in MDR PA101885 after about 6 h of incubation. For WT PAO1, there was re-growth after 24 h of incubation with 4 μg/ml (i.e. MIC) of aztreonam alone, but not in combination with compound 2 (FIG. 7A), thus reflecting a synergistic relationship after 24 h. Similarly, there was re-growth after 24 h incubation of MDR PA101885 with 8 μg/ml of aztreonam alone but not in combination with compound 2 (FIG. 7B). Treatment of PAO1 with 1 μg/ml (i.e. MIC) of meropenem, alone and in combination with compound 2, resulted in a re-growth after 24 h of incubation. A synergistic relationship was observed between meropenem and compound 2 in MDR PA101885 isolate, but not wild-type PAO1 (FIG. 7), an effect that is consistent with the degree of potentiation seen in checkerboard assay (Tables 2 and 3). Re-growth of PA101885, in the presence of 8 μg/ml aztreonam alone, started after 3 h and the synergistic relationship between aztreonam and compound 2 was apparent as early as 6 h post inoculation. On the other hand, re-growth of MDR PA101885 in the presence of 1 μg/ml meropenem alone started after 6 h and its synergistic relationship with compound 2 was evident at 6 h (FIG. 7B). Overall, the ability of compound 2 to potentiate the bacteria-killing properties of aztreonam and meropenem is both time- and concentration-dependent. The interaction between aztreonam and compound 2 was synergistic against both WT PAO1 and MDR PA101885, while the interaction between meropenem and compound 2 was synergistic against PA101885 but indifferent against PAO1. In the presence of compound 2, there was no regrowth of both strains after 24 h of incubation with aztreonam while there was regrowth in both after 24 h of incubation with meropenem.

Triple Combination Therapy.

Figure 8:
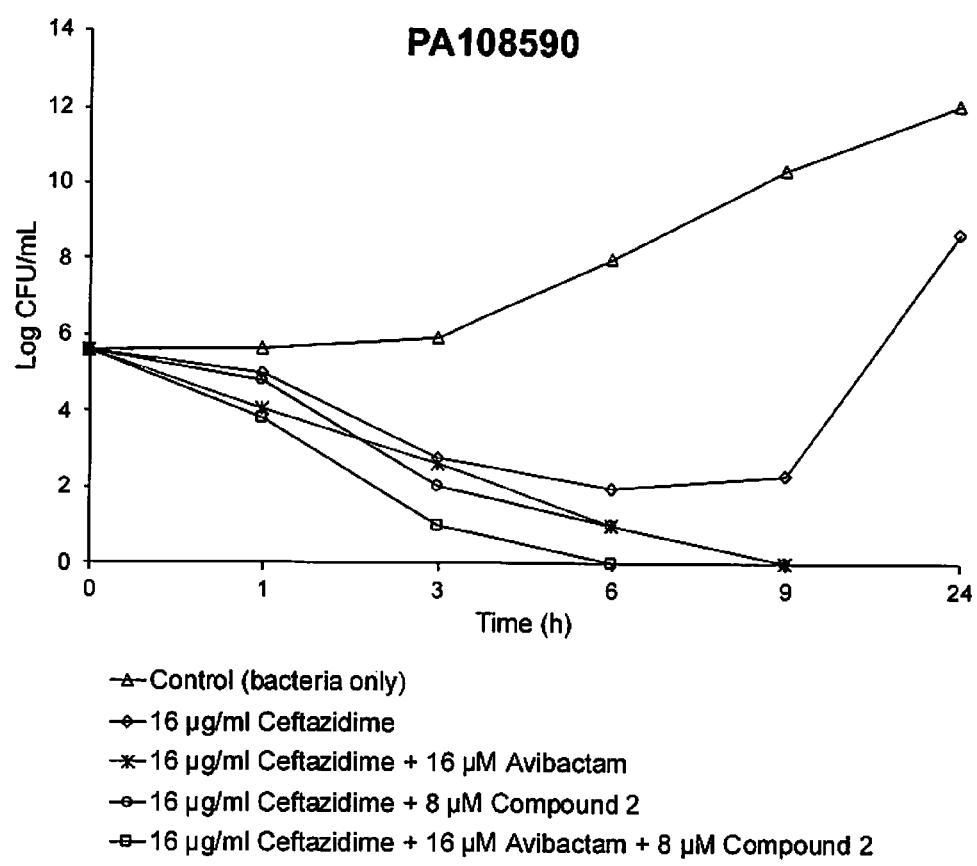
FIG. 8. Triple combination time-kill kinetics of ceftazidime+avibactam+compound 2 on the viability of multidrug resistant *P. aeruginosa* 108590. MIC of ceftazidime is 32 μg/mL. Dashed black line stands for a 3-Log reduction in total CFU/mL from original inoculum while dashed red line represents the limit of detection for the study. Each data point is an average of three independent determinations.

MDR PA108590, which had a lag phase of about 3 h in LB media (FIG. 8), was used for this study because of its high susceptibility to enzymatic inhibition by avibactam (FIG. 6). Ceftazidime and avibactam were studied at a ratio of 4 parts to 1 part, the typical therapeutic ratio used clinically. At 16 μg/mL, i.e. half MIC, ceftazidime alone exhibited bactericidal effects after 3 h while a combination of ceftazidime (16 μg/mL) and avibactam (16 μM, i.e. 4 μg/mL) resulted in a significant reduction in bacterial load count (~2-Log lower than ceftazidime alone) within 1 h (FIG. 8). After 3 h of incubation, the bacterial counts of ceftazidime alone and ceftazidime+avibactam were similar, suggesting the possibility of β-lactamase enzyme saturation by avibactam. Conversely, the bacterial counts of ceftazidime+avibactam+compound 2 was identical to that of ceftazidime+avibactam after 1 h but significantly lower (>2-Log difference) after 3 h (FIG. 8). This implies that whereas avibactam exhibited a rapid synergistic effect with ceftazidime after 1 h, compound 2 further potentiated the effect of this combination within 3 h. Indeed, the bacteria culture was completely sterilized within 3 h when treated with a triple combination of ceftazidime, avibactam, and compound 2 (limit of detection=10 CFU/mL), an effect that represents ~6-Log reduction in the total CFU/mL from the original inoculum (FIG. 8). There was re-growth of PA108590 after 9 h of incubation with 16 μg/mL ceftazidime alone, but not with the double (i.e. ceftazidime+avibactam, or ceftazidime+compound 2) or triple (i.e. ceftazidime+avibactam+compound 2) combinations. In summary, ceftazidime and avibactam exhibited synergistic effect within 1 h and sterilized the bacteria culture within 6 h, while compound 2 further potentiates this combination, leading to culture sterilization within 3 h.

Example 9—In Vivo Efficacy Studies Using *Galleria mellonella* Infection Model

In vitro and in vivo discordances have been observed in antimicrobial chemotherapy, thus, therapeutic efficacy may not necessarily be reliably extrapolated based on in vitro data alone. To investigate whether the in vitro synergistic relationships observed between compound 2 and β-lactam antibiotics is translated in vivo, we examined the ability of different concentrations of mono- and combination therapies to offer therapeutic protection to MDR *P. aeruginosa*-infected *Galleria mellonella* wax worms. Multiple reports have demonstrated the suitability of this infection model to determine virulence of bacterial strains, as well as efficacy and pharmacokinetics of antimicrobial agents (13, 20, 22, 53, 54). Preliminary studies were done to determine the maximum tolerable doses of aztreonam, meropenem, ceftazidime, avibactam, and compound 2, by injecting high concentrations (100 mg/kg and 200 mg/kg each) into the larvae and survivability scored for up to 4 days (FIG. 9a). Colistin (100 mg/kg), an antibiotic well known for its toxicity towards eukaryotes, served as a positive control for this experiment while PBS served as negative control. 100% survival was recorded in all groups injected with 100 mg/kg and 200 mg/kg of test compounds after 48 h, except the colistin group where only 30% survival was recorded when exposed to 100 mg/kg colistin (FIG. 9a). Survivability was scored for a total of 4 days. The results indicate that the test compounds were not toxic to the larvae, an effect that is consistent with in vitro toxicity studies (vide infra). Colistin-induced larvae death is also consistent with the toxicological liabilities of this drug. Furthermore, an inoculum size of approximately 5 CFU of MDR PA 101885 and PA108590 was found suitable to induce 100% mortality of the larvae after 12-18 h.

Double Combination Therapy.

Figure 9:
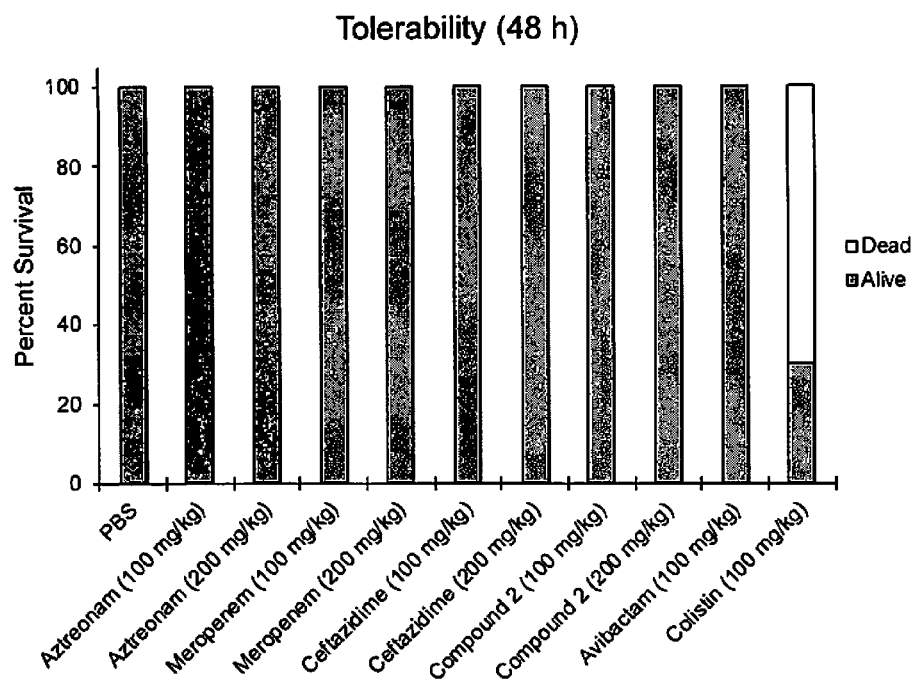
FIG. 9. In vivo dose-dependent tolerability and efficacy of combination therapies of compound 2 with aztreonam (AZT), meropenem (MER), ceftazidime (CAZ), or ceftazidime-avibactam (CAZ-AVI) demonstrated in *Galleria mellonella* infection model. a) Tolerable doses were determined by injecting 100 and 200 mg/kg of test compounds alone into the larvae and survivability was scored for 48 h (4 days). b) Efficacy studies using a single dose administration of different concentrations of mono- and double combination therapies to treat PA1-01885-challenged larvae 3 h post infection. Survivability of the larvae was scored every 6 h for 36 h, c) Efficacy studies using a single dose administration of ceftazidime (CAZ), avibactam (AVI), or compound 2, alone or in combination, to treat PA108590-challenged larvae 3 h post infection. Survivability of the larvae was scored every 6 h for 48 h.
Figure 1:
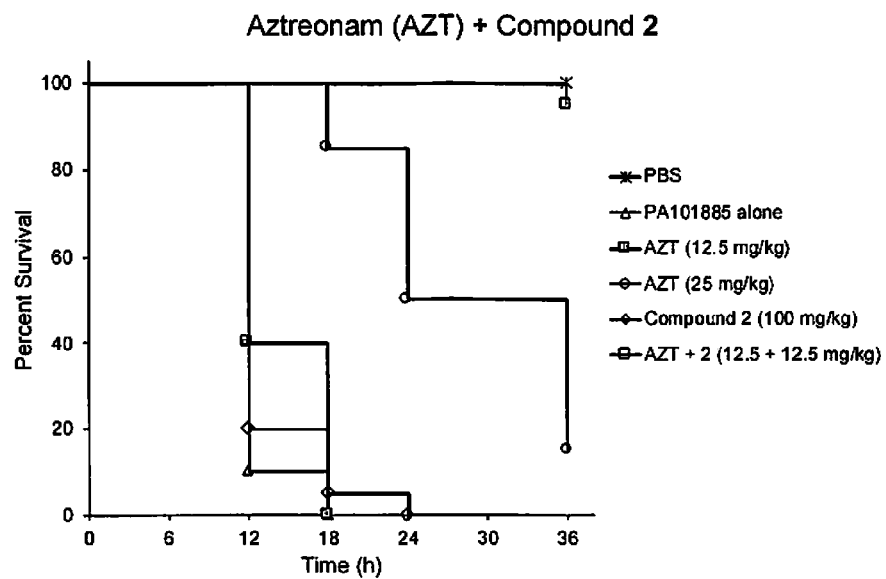
Figure 9:
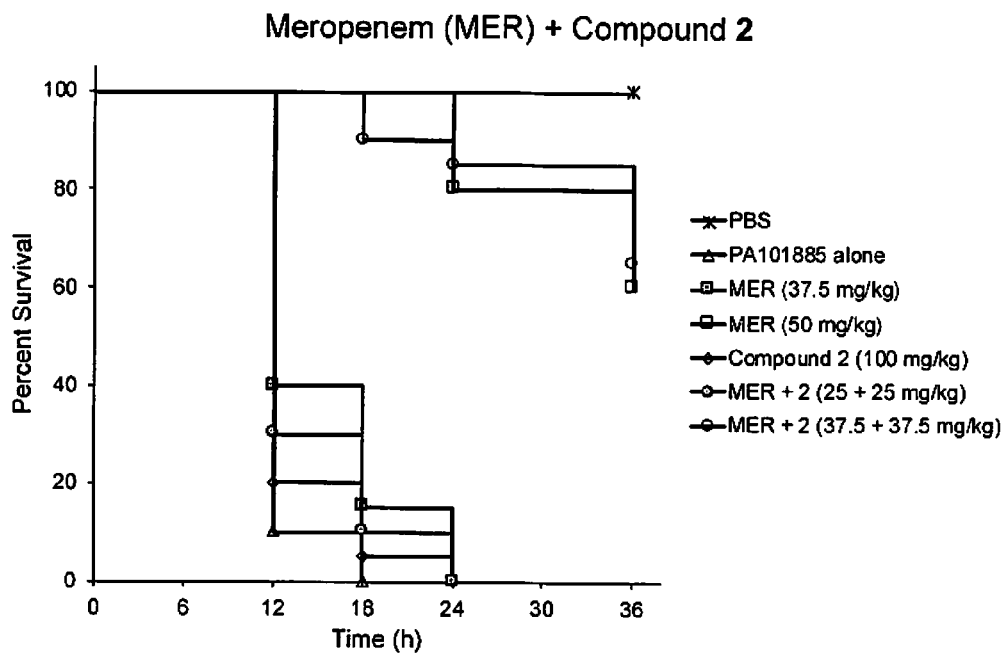
Figure 2:
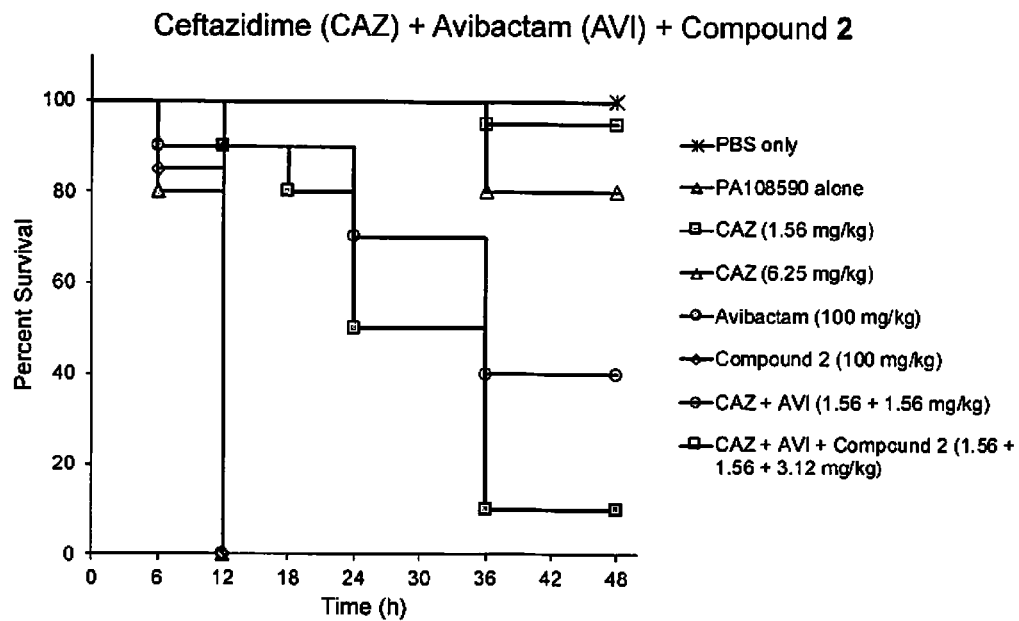

The ability of aztreonam or meropenem, alone and in combination with compound 2, to protect the larvae from MDR PA101885 3 h post infection was determined. A 12.5 mg/kg single dose of aztreonam resulted in 100% mortality after 18 h while a single dose of 25 mg/kg aztreonam resulted in 50% survival after 24 h (FIG. 9b). However, a single dose combination of 12.5+12.5 mg/kg of aztreonam and compound 2 resulted in 100% survival after 24 h (FIG. 7b). Similarly, a single dose of 37.5 mg/kg or 50 mg/kg meropenem resulted in 0% and 80% survival, respectively, after 24 h, while a combination therapy of meropenem and compound 2, 25+25 mg/kg or 37.5+37.5 mg/kg, resulted into 0% and 85% survival, respectively, after 24 h (FIG. 9b). These data clearly show that the therapeutic effects of the antibiotics alone, as well as in combination with compound 2, are dose-dependent. The therapeutic benefit of a 12.5+12.5 mg/kg of aztreonam+compound 2 combination is superior to a 25 mg/kg aztreonam monotherapy, while that of a 37.5+37.5 mg/kg meropenem/compound 2 combination is greater than a 50 mg/kg meropenem monotherapy. It should be noted that compound 2 by itself is innately inactive against MDR PA101885 isolate in vitro and in vivo (FIG. 9). This unequivocally demonstrates the ability of compound 2 to potentiate the antimicrobial effects of aztreonam and meropenem, as well as offer therapeutic protection to PA101885-challenged larvae at clinically achievable concentrations. High concentrations (100 mg/kg each) of aztreonam or meropenem served as the positive controls for this experiment while treatment with PBS only served as negative control.

Triple Combination Therapy.

Next, we investigated the therapeutic superiority of a triple combination therapy (ceftazidime+avibactam+compound 2) over a traditional β-lactam/β-lactamase inhibitor combination (ceftazidime+avibactam) in the *G. mellonella* infection model.

The larvae were challenged with MDR PA108590, a β-lactamase-harboring strain that is susceptible to β-lactamase enzyme inhibition by avibactam (FIGS. 6 and 8), for 3 h and subsequently treated with different concentrations of ceftazidime, avibactam, or compound 2, alone and in combination. A 1.56 mg/kg single dose of ceftazidime resulted in 50% and 10% survival of the worms after 24 h and 36 h, respectively, while a single dose administration of 1.56+1.56 mg/kg of ceftazidime+avibactam resulted in 70% and 40% survival after 24 h and 36 h, respectively (FIG. 9*c*). However, a single dose combination of 1.56+1.56+3.12 mg/kg of ceftazidime+avibactam+compound 2 resulted in 100% and 95% survival after 24 h and 36 h, respectively (FIG. 9*c*). This demonstrates that the in vitro benefits of the triple combination therapy translate in vivo, and that compound 2 further potentiates the therapeutic effects of ceftazidime-avibactam combination, thus protecting the larvae from MDR PA108590.

Example 10—Cytotoxicity and Hemolytic Studies

Figure 10:
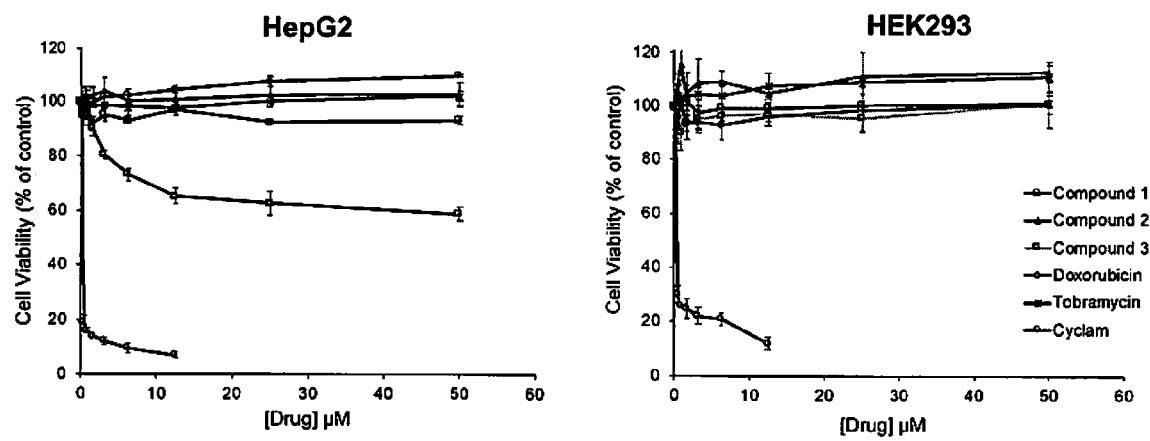
FIG. 10. Cytotoxicity of compounds 1-3, doxorubicin, tobramycin, and cyclam against human liver carcinoma (HepG2) cells and human embryo kidney (HEK293) cells using PrestoBlue cell viability assay. Doxorubicin was used as positive control. Error bars denote standard deviation of at least four replicates. b) Hemolytic activity of compounds 1-3 evaluated against swine erythrocytes at different concentrations. 0.1% Triton X-100 (100% hemolysis) was used as positive control to calculate percent hemolysis. The result represents the mean of three independent determinations.
Figure 10:
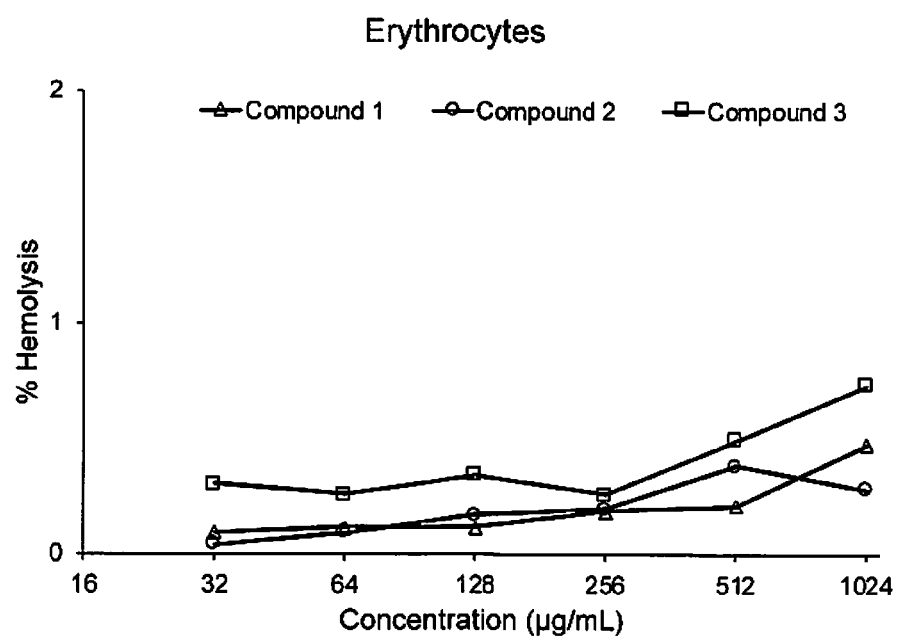

Chelating agents, such as EDTA, which disrupt the OM by removing $Mg^{2+}$ and $Ca^{2+}$ have for long been known as effective permeabilizers (30). However, most of these agents are not used clinically because of their toxicological liabilities in humans. To establish the in vitro toxicity profiles of compounds 1-3 against eukaryotic cells, they were screened against human liver (HepG2) and kidney (HEK293) cells, as well as porcine erythrocytes, at different concentrations. For cytotoxicity against human cells, doxorubicin, a very potent anticancer drug, was used as a positive control for this experiment (55). The results of the study showed that none of the tobramycin-cyclam conjugates 1-3 was toxic to both HepG2 and HEK293 cell lines (FIG. 10*a*). The viability of both cells remained at >90% at the highest concentration (50 μM) of the compounds tested, except for compound 3 against HepG2, where cell viability was about 60% at 50 μM (FIG. 10*a*). The effective adjuvant concentrations of these compounds are ≤10 μM, indicating an appreciably wide therapeutic window in vitro. Expectedly, doxorubicin reduced the cytotoxicity of HepG2 and HEK293 cells to less than 10% at about 12 μM (6.5 μg/mL) (FIG. 10*a*), consistent with its cytotoxic properties. For toxicity against freshly collected porcine erythrocytes, 0.1% Triton X-100 served as the positive control and was used to calculate percent hemolysis. Compounds 1-3 exhibited insignificant hemolytic effects (<1%) at very high concentrations of 1024 μg/mL (FIG. 10*b*), a 64-fold higher dose than the maximum synergistic concentration used in the study. In vivo toxicity was also assessed in *G. mellonella* worms and the results revealed 100% survival of the worms when exposed to 100 or 200 mg/kg of compound 2 for 2 days (FIG. 9*a*).

EXPERIMENTAL SECTION

Chemistry. All chemicals and reagents were purchased from Sigma-Aldrich (Oakville, ON, Canada) except tobramycin that was purchased from AK Scientific Inc. (CA, USA). The chemicals were all used without further purification. Air and moisture-sensitive reactions were performed with dry solvents under nitrogen atmosphere. Thin-layer chromatography (TLC) was carried out on aluminum-backed silica gel 60 $F_{254}$ GF plates (0.25 mm) and/or aluminum-backed reverse phase silica gel 60 RP-18 $F_{254}S$ plates (Merck KGaA, Germany) with the indicated solvents, and visualized by staining within ninhydrin solution in n-butanol. Intermediate compounds were purified by flash chromatography on silica gel 60 (230-400 ASTM mesh) and final compounds were purified on reverse-phase C18 silica gel (Silicyle, USA). Yields refer to chromatography-purified homogenous materials, except otherwise stated. $^1H$ and $^{13}C$ NMR spectra were recorded on Bruker AMX-300 and AMX-500 spectrometers (Germany) as solutions and reported in the order of chemical shifts (δ) in ppm relative to the indicated solvent, multiplicity (s, singlet; d, doublet; t, triplet and m, multiplet), number of protons, and coupling constants (J) in hertz (Hz). $^1H$ and $^{13}C$ of compounds were assigned using 1D and 2D NMR experiments such as Proton, COSY, Carbon-13, DEPT-135, HSQC, and HMBC. ESI-MS and MALDI-TOF MS analyses were performed on Varian 500-MS ion trap mass spectrometer (USA) and Bruker Daltonics Ultraflextreme MALDI TOF/TOF mass spectrometer (Germany), respectively. The purity of final compounds as determined by elemental analysis was >95%.

General Procedure A: 5-O-alkylation of Boc and TBDMS protected Tobramycin for the Preparation of Compounds 13a-c. A solution of 12 (1 equiv.) in toluene was treated with KOH (3 equiv.), 1,n-dibromoalkane (3 equiv.), and a catalytic amount of tetrabutylammonium hydrogen sulphate, TBAHS (0.1 equiv.). The reaction mixture was stirred at RT overnight, dispersed in water and extracted with an equal volume of ethyl acetate (×3). The organic layers were combined, washed with brine (×1), dried over anhydrous $Na_2SO_4$ and concentrated in vacuo. The crude products were then purified by column chromatography (hexanes/ethyl acetate, 12:1 to 10:1, v/v) to afford compounds 13a-c as white solids.

General Procedure B: Hydroxylation of 5-O-(n-Bromoakyl)-1,3,2',6',3''-penta-N-Boc-4',2'',4'',6''-tetra-O-TBDMS-tobramycin for the Preparation of Compounds 14a-c. A solution of compounds 13a-c (1 equiv.) in a mixture of DMF (20.0 mL) and water (2.0 mL) was treated with $Cs_2CO_3$ (2 equiv.) and stirred overnight at 70° C. The crude mixture was then dispersed in water and extracted with ethyl acetate (50 mL×3). The combined organic layer was washed with saturated brine (×1), dried over anhydrous $Na_2SO_4$, concentrated in vacuo, and purified by flash chromatography (hexanes/ethyl acetate, 10:1 to 8:1, v/v) to afford compounds 14a-c as white solids.

General Procedure C: Oxidation of 5-O-(n-Hydroxyldodecyl)-1,3,2',6',3''-penta-N-Boc-4',2'',4'',6''-tetra-O-TBDMS-tobramycin to Aldehydes for the Preparation of Compounds 15a-c. Compounds 14a-c (1 equiv.) dissolved in dry DCM were treated with PCC (pyridimin chlorochromate, 3 equiv.) in the presence of NaOAc, and stirred under nitrogen gas for 3 h at RT. The resulting crude was filtered through a pad of silica and concentrated under reduced pressure to give compounds 15a-c. These compounds were used immediately without further purification.

General Procedure D: Reductive Amination of Aldehydes with (Boc)$_3$-protected Cyclam for the Preparation of Compounds 16a-c. A solution of compounds 15a-c (1 equiv.) in dry DCE was treated with (Boc)$_3$-protected cyclam 10 (1.5 equiv.) and two drops of acetic acid. The reaction was stirred for 7 h at RT under nitrogen gas. The reaction mixture was the cooled in ice, treated with Na(OAc)$_3$BH (3 equiv.), and stirred overnight under nitrogen atmosphere from 0° C. to RT. The resulting mixture was quenched with saturated Na$_2$CO$_3$, extracted with DCM (×3), concentrated in vacuo, and purified by flash chromatography (hexanes/ethyl acetate, 10:1 to 4:1, v/v) to yield compounds 16a-c.

General Procedure E: Deprotection of Hydroxyls and Amines (Removal of TBDMS and Boc Protecting Groups) for Preparation of Compounds 1-3. A solution of TBDMS- and Boc-protected compounds 16a-c in anhydrous THF (5.0 mL) were treated with tetrabutylammonium fluoride (TBAF, 6 equiv.) and stirred under nitrogen atmosphere for 2 h. The reaction mixture was concentrated under vacuo, dissolved in water and extracted with DCM (×3). The organic layers were combined, dried over anhydrous Na$_2$SO$_4$, concentrated in vacuo, and purified by column chromatography (hexanes/ethyl acetate, 1:1, v/v, then dichloromethane/methanol, 25:1 to 20:1, v/v). A solution of the resulting compounds in DCM (2.0 mL) were further treated with trifluoroacetic acid (2.0 mL), stirred at RT for 1 h and concentrated under low vacuo. 2% methanol in diethylether (2.0 mL) was then added, stirred gently for 1 min and the solvent carefully decanted to give off-white solid compounds. The crude products were subsequently purified by reverse-phase flash chromatography (eluted with 100% deionized water) to afford analytically pure compounds 1-3 as off-white TFA salt solid compounds.

5-O-(Butylcyclam)-tobramycin.9TFA (1). Compound 16a was deblocked according to general procedure E. $^1$H NMR (500 MHz, D$_2$O) δ 5.36 (d, J=2.5 Hz, 1H, anomeric), 5.15 (d, J=3.4 Hz, 1H, anomeric), 4.25 (dd, J=9.4, 3.6 Hz, 1H), 4.11 (t, J=9.7 Hz, 1H), 3.83-3.52 (m, 12H), 3.51-3.20 (m, 19H), 3.19-3.10 (m, 3H), 2.38 (dd, J=12.7, 4.4 Hz, 1H), 2.15-2.07 (m, 2H), 2.07-1.98 (m, 4H), 1.79 (m 1H), 1.71-1.60 (m, 2H), 1.57-1.49 (m, 2H). $^{13}$C NMR (126 MHz, D$_2$O) δ 101.0 (anomeric), 92.8 (anomeric), 82.3, 81.6, 77.1, 76.1, 73.2, 72.1, 68.6, 64.9, 63.1, 59.4, 55.8, 54.9, 49.5, 48.3, 47.7, 47.3, 44.7, 41.5, 40.9, 40.8, 38.4, 37.4, 36.6, 28.0, 27.7, 26.4, 20.5, 18.4, 17.6. MALDI TOF-MS nee calcd for C$_{32}$H$_{68}$N$_9$O$_9$, 722.514; measured m/e, 722.519 [M+H]$^+$.

5-O-(Octylcyclam)-tobramycin.9TFA (2). Compound 16b (0.068 g, 0.04 mmol) was deblocked according to general procedure E to give 2 as a white solid (0.06 g, 78%). $^1$H NMR. (500 MHz, D$_2$O) δ 5.26 (d, J=2.6 Hz, 1H, anomeric), 5.03 (d, J=3.5 Hz, 1H, anomeric), 4.15 (dd, J=8.6, 3.8 Hz, 1H), 4.01 (m, 1H), 3.85-3.54 (m, 11H), 3.54-3.33 (m, 13H), 3.32-3.23 (m, 7H), 3.21-3.14 (m, 3H), 2.42 (dd, J=12.7, 4.4 Hz, 1H), 2.16-2.09 (m, 2H), 2.11-2.01 (m, 4H), 1.82 (m, 1H), 1.68-1.59 (m, 2H), 1.56-1.44 (m, 2H), 1.28-1.09 (m, 8H). $^{13}$C NMR (126 MHz, D$_2$O) δ 101.3 (anomeric), 92.7 (anomeric), 81.9, 81.9, 76.8, 75.8, 73.7, 73.1, 68.5, 64.7, 63.1, 59.2, 56.1, 54.8, 49.7, 48.3, 47.5, 47.3, 44.2, 41.3, 40.7, 40.7, 38.4, 37.2, 37.1, 36.3, 29.4, 28.8, 28.3, 28.0, 27.7, 25.6, 25.1, 24.0, 18.2, 17.4. MALDI TOF-MS m/e calcd for C$_{36}$H$_{76}$N$_9$O$_9$, 778.577; measured m/e, 778.579 [M+H]$^+$.

5-O-(Dodecylcyclam)-tobramycin.9HCl (3). Compound 16c (0.044 g, 0.03 mmol) was deblocked according to general procedure E and the resulting compound was treated with stoichiometric amount of aqueous HCl solution to give 3 as a white solid HCl salt (0.046 g, 91%). 1H NMR (500 MHz, D$_2$O) δ δ 5.22 (d, J=2.6 Hz, 1H, anomeric), 4.99 (d, J=3.5 Hz, 1H, anomeric), 4.11 (dd, J=9.3, 3.8 Hz, 1H), 3.97 (t, J=9.8 Hz, 1H), 3.82-3.50 (m, 11H), 3.48-2.98 (m, 23H), 2.37 (dd, J=12.6, 4.4 Hz, 1H), 2.12-2.05 (m, 2H), 2.03-1.90 (m, 4H), 1.77 (m, 1H), 1.60-1.52 (m, 2H), 1.51-1.39 (m, 2H), 1.24-1.06 (m, 16H). $^{13}$C NMR (126 MHz, D$_2$O) δ 101.4 (anomeric), 92.8, 82.0, 81.9, 76.9, 76.0, 73.9, 73.2, 68.6, 64.8, 63.1, 59.2, 55.4, 54.8, 49.7, 48.4, 48.0, 47.3, 44.9, 41.8, 41.4, 41.1, 38.4, 37.84, 37.81, 37.1, 29.5, 29.0, 29.0, 28.9, 28.8, 28.7, 28.3, 28.1, 27.7, 25.7, 25.4, 23.8, 18.9, 18.0. MALDI TOF-MS m/e calcd for C$_{40}$H$_{84}$N$_9$O$_9$, 834.639; measured m/e, 834.640 [M+H]$^+$.

(Boc)$_3$-cyclam (10). Synthesis was accomplished following previously reported procedure (76). 1,4,8,11-tetraazacyclotetradecane (cyclam 9) (0.35 g, 1.75 mmol) was dissolved in DCM (5.0 mL). Di-tert-butoxy-dicarbonate (Boc$_2$O) (1.0 mL, 4.35 mmol) was dissolved separately in DCM (5.0 mL) and added dropwise over 15 mins and allowed to stir overnight. The reaction mixture was concentrated, re-dispersed in hexanes (45.0 mL) and the insoluble were filtered. The solvent was removed in vacuo and purified by flash chromatography (ethyl acetate/hexanes, 4:1, v/v) to afford compound 10 (0.67 g, 92%) as white foam. $^1$H NMR (300 MHz, CDCl$_3$) δ 3.48-3.19 (m, 12H), 2.78 (t, J=5.3 Hz, 2H), 2.61 (t, J=5.6 Hz, 2H), 2.01-1.81 (m, 2H), 1.76-1.63 (m, 2H), 1.45 (m, 27H, Boc). $^{13}$C NMR (75 MHz, CDCl$_3$) δ 156.31, 155.48, 79.46, 60.35, 50.56, 50.02, 47.68, 46.73, 45.87, 44.07, 28.51, 28.49, 21.02, 14.19. ESI-MS: m/z calcd for C25H49N4O6Na$^+$, 501.7; found 502.0 [M+Na]$^+$.

1,3,2',6',3"-penta-N-Boc-4',2",4",6"-tetra-O-TBDMS-tobramycin (12). Commercial tobramycin (0.50 g, 1.01 mmol) was dissolved in a 2:1 mixture of methanol and water (75.0 mL) and treated with Boc$_2$O (1.63 g, 7.49 mmol) in the presence of Et$_3$N (1.0 mL). The reaction mixture was stirred under reflux (at 55° C.) overnight, concentrated under vacuo and thoroughly dried under high vacuum for 24 h to afford a white powdery solid (1.04 g, 100%). The dried crude penta-N-boc-protected tobramycin (1.04 g, 1.07 mmol) was dissolved in anhydrous DMF (6.0 mL) and treated with tert-butyldimethysilyl chloride, TBDMSCl (1.13 g, 7.49 mmol) and N-methylimidazole (0.6 mL). The reaction was stirred at RT for 4 days under nitrogen gas atmosphere, and the resulting mixture was poured into water (50.0 mL) and extracted with DCM (×3). The organic layer was dried over anhydrous Na$_2$SO$_4$, concentrated in vacuo, and purified by flash chromatography using gradient elution (hexanes/ethyl acetate, 15:1 to 8:1, v/v) to afford 16 (1.05 g, 67%) as a white solid. NMR data are consistent with an earlier report (20).

5-O-(n-Bromoalkyl)-1,3,2',6',3"-penta-N-Boc-4',2",4", 6"-tetra-O-TBDMS-tobramycin (13a-c). Compounds 13a, 13b, and 13c were prepared by treating 12 with 1,4-dibromobutane, 1,8-dibromooctane, and 1,12-dibromododecane, respectively, according to general procedure A.

5-O-(4-Bromobutyl)-1,3,2',6',3"-penta-N-Boc-4',2",4", 6"-tetra-O-TBDMS-tobramycin (13a). Yield (47%). $^1$H NMR (300 MHz, CDCl$_3$) δ 5.24-5.12 (m, 2H, anomeric), 4.28-4.09 (m, 3H), 3.93-3.14 (m, 17H), 2.61-2.37 (m, 1H), 2.14-1.84 (m, 5H), 1.72-1.56 (m, 3H), 1.61-1.35 (m, 45H, Boc), 1.11-0.72 (m, 36H, TBDMS, tert-butyl), 0.24-0.09 (m, 24H, TBDMS-CH$_3$). ESI-MS: m/z calcd for C$_{71}$H$_{140}$BrN$_5$O$_{19}$Si$_4$Na+, 1583.2; found 1583.2 [M+Na]$^+$.

5-O-(8-Bromooctyl)-1,3,2',6',3"-penta-N-Boc-4',2",4", 6"-tetra-O-TBDMS-tobramycin (13b). Yield (51%). $^1$H NMR (300 MHz, CDCl$_3$) δ 5.26-5.12 (m, 2H, anomeric), 4.39-3.97 (m, 3H), 3.89-3.07 (m, 16H), 2.47 (d, J=12.8 Hz, 1H), 2.08-1.94 (m, 2H), 1.93-1.77 (m, 2H), 1.65 (m, 1H), 1.56-1.39 (m, 45H, Boc), 1.39-1.14 (m, 8H), 1.13-1.02 (m, 1H), 1.05-0.75 (m, 36H, TBDMS tert-butyl), 0.34-0.15 (m, 24H TBDMS-CH$_3$). ESI-MS: m/z calcd for C$_{75}$H$_{148}$BrN$_5$O$_{19}$Si$_4$Na+, 1613.90; found 1613.94 [M+Na]$^+$.

5-O-(12-Bromododecyl)-1,3,2',6',3"-penta-N-Boc-4',2", 4",6"-tetra-O-TBDMS-tobramycin (13b). Yield (73%). $^1$H NMR (300 MHz, CDCl$_3$) δ 5.31-515 (m, 2H, anomeric), 4.36-4.01 (m, 3H), 3.93-3.07 (m, 17H), 2.58-2.35 (m, 1H), 2.13-1.98 (m, 1H), 1.98-1.72 (m, 3H), 1.53-1.38 (m, 45H, Boc), 1.38-1.23 (m, 19H), 1.05-0.80 (m, 36H, TBDMS tert-butyl), 0.27-0.03 (m, 24H, TBDMS-CH$_3$). $^{13}$C NMR (75 MHz, CDCl$_3$) δ 85.77, 79.42, 79.24, 57.27, 50.52, 34.06, 32.88, 32.83, 31.60, 30.67, 30.05, 29.67, 29.58, 29.47, 29.44, 28.82, 28.66, 28.52, 28.42, 28.22, 28.18, 26.16, 26.04, 26.01, 25.80, 18.52, 18.36, 18.12, 17.93, −3.38, −3.77, −4.17, −4.93, −5.06, −5.21. ESI-MS: m/z calcd for C$_{79}$H$_{156}$BrN$_5$O$_{19}$Si$_4$Na+, 1692.955; found 1692.972 [M+Na]$^+$.

5-O-(n-Hydroxylalkyl)-1,3,2',6',3''-penta-N-Boc-4',2'',4'',6''-tetra-O-TBDMS-tobramycin (14a-c). Compounds 14a-c were prepared by treating compounds 13a-c with Cs$_2$CO$_3$ in aqueous conditions, according to general procedure B.

5-O-(4-Hydroxylbutyl)-1,3,2',6',3''-penta-N-Boc-4',2'',4'',6''-tetra-O-TBDMS-tobramycin (14a). Yield (27%). $^1$H NMR (300 MHz, CDCl$_3$) δ 5.31-5.16 (m, 2H, anomeric), 4.74-4.51 (m, 1H), 4.27-3.93 (m, 2H), 3.92-3.07 (m, 17H), 2.55-2.32 (m, 1H), 2.28-2.12 (m, 1H), 2.09-1.93 (m, 1H), 1.74-1.53 (m, 4H), 1.49-1.30 (m, 45H, Boc), 1.00-0.80 (m, 36H, TBDMS), 0.21-0.03 (m, 24H, TBDMS). ESI-MS m/z calcd for C$_{71}$H$_{141}$N$_5$O$_{20}$Si$_4$Na+, 1518.9; found 1519.2 [M+Na]$^+$ 5-O-(8-Hydroxyloctyl)-1,3,2',6',3''-penta-N-Boc-4',2'',4'',6''-tetra-O-TBDMS-tobramycin (14b). Yield (30%). $^1$H NMR (300 MHz, CDCl$_3$) δ 5.26-5.12 (m, 2H), 4.30-4.02 (m, 3H), 3.87-3.06 (m, 16H), 2.44 (d, J=12.5 Hz, 1H), 2.22 (s, 1H), 2.06-1.92 (m, 2H), 1.59 (m, 1H), 1.52-1.33 (m, 45H, Boc), 1.30-1.18 (m, 8H), 1.12-0.99 (m, 1H), 1.00-0.72 (m, 36H, TBDMS tert-butyl), 0.21-0.20 (m, 24H, TBDMS-CH$_3$). C$_{75}$H$_{149}$N$_5$O$_{20}$Si$_4$Na+, 1575.0; found 1575.4 [M+Na]$^+$.

5-O-(12-Hydroxyldodecyl)-1,3,2',6',3''-penta-N-Boc-4',2'',4'',6''-tetra-O-TBDMS-tobramycin (14c). Yield (39%). $^1$H NMR (300 MHz, CDCl$_3$) δ 5.31-515 (m, 2H, anomeric), 4.36-4.01 (m, 3H), 3.93-3.07 (m, 17H), 2.58-2.35 (m, 1H), 2.13-1.98 (m, 1H), 1.98-1.72 (m, 3H), 1.53-1.38 (m, 45H, Boc), 1.38-1.23 (m, 19H), 1.05-0.80 (m, 36H, TBDMS tert-butyl), 0.27-0.03 (m, 24H, TBDMS-CH$_3$). ESI-MS: m/z calcd for C$_{79}$H$_{157}$N$_5$O$_{20}$Si$_4$Na+, 1631.0; found 1631.5 [M+Na]$^+$.

5-O-(n-Alkanal)-1,3,2',6',3''-penta-N-Boc-4',2'',4'',6''-tetra-O-TBDMS-tobramycin (15a-c). Compounds 15a-c were prepared by treating compounds 14a-c with pyridinium chlorochromate, according to general procedure C.

5-O-(12-Dodecanal)-1,3,2',6',3''-penta-N-Boc-4',2'',4'',6''-tetra-O-TBDMS-tobramycin (15c). Yield (85%). $^1$H NMR (300 MHz, CDCl$_3$) δ 9.71 (s, 1H, aldehyde), 5.23-4.58 (m, 2H), 4.21-3.95 (m, 4H), 3.91-2.95 (m, 14H), 2.45-2.28 (m, 2H), 2.03-1.96 (m, 4H), 1.64-1.35 (m, 45H, Boc), 1.25-0.99 (m, 20H), 1.04-0.79 (m, 36H, TBDMS tert-butyl), 0.31-0.13 (m, 24H, TBDMS-CH$_3$).

5-O-[alkyl-(Boc)$_3$-cyclam]-1,3,2',6',3''-penta-N-Boc-4',2'',4'',6''-tetra-O-TBDMS-tobramycin (16a-c). Compounds 16a-c were prepared by treating compounds 15a-c each with (Boc)$_3$-cyclam 10 via reductive amination, according to general procedure D.

5-O-[Butyl-(Boc)$_3$-cyclam]-1,3,2',6',3''-penta-N-Boc-4',2'',4'',6''-tetra-O-TBDMS-tobramycin (16a). $^1$H NMR (300 MHz, CDCl$_3$) δ 5.25-5.08 (m, 2H, anomeric), 5.05-4.93 (m, 1H), 4.89-4.68 (m, 1H), 4.26-4.06 (m, 2H), 3.87-3.11 (m, 26H), 2.63-2.28 (m, 7H), 2.03-1.77 (m, 3H), 1.68-1.21 (m, 80H), 0.97-0.79 (m, 36H, TBDMS tert-butyl), 0.25-0.14 (m, 24H, TBDMS-CH$_3$). $^{13}$C NMR (75 MHz, CDCl$_3$) δ 155.63, 154.67, 79.50, 79.32, 57.15, 50.70, 48.26, 46.93, 35.77, 28.64, 28.54, 28.50, 28.44, 26.13, 26.01, 25.79, 18.48, 18.30, 18.08, 17.91, −3.31, −3.72, −4.17, −4.86, −4.91, −4.99, −5.14. ESI-MS: m/z calcd for C$_{96}$H$_{188}$N$_9$O$_{25}$S$_4$$^+$, 1980.3; found 1681.3 [M+H]$^+$.

5-O-[Octyl-(Boc)$_3$-cyclam]-1,3,2',6',3''-penta-N-Boc-4',2'',4'',6''-tetra-O-TBDMS-tobramycin (16b). $^1$H NMR (300 MHz, CDCl$_3$) δ 5.21 (m, 1H, anomeric), 5.17-5.10 (m, 1H, anomeric), 5.12-4.94 (m, 1H), 4.77 (m, 1H), 4.34-3.98 (m, 3H), 3.91-3.04 (m, 26H), 2.63-2.27 (m, 6H), 2.11 (m, 1H), 2.07-1.95 (m, 3H), 1.95-1.81 (m, 2H), 1.71-1.60 (m, 2H), 1.57-1.30 (m, 76H, Boc), 1.28-1.18 (m, 9H), 1.12-1.00 (m, 1H), 0.99-0.79 (m, 36H, TBDMS ten-butyl), 0.30-0.11 (m, 24H, TBDMS-CH$_3$). $^{13}$C NMR (75 MHz, CDCl$_3$) δ 155.67, 154.72, 79.31, 79.24, 60.34, 48.38, 35.68, 30.29, 29.78, 28.64, 28.53, 28.50, 28.41, 27.93, 26.14, 26.03, 26.00, 25.78, 21.01, 18.48, 18.33, 18.10, 17.91, 14.18, −3.78, −4.19, −4.88, −5.16. ESI-MS: m/z calcd for C$_{100}$H$_{195}$N$_9$O$_{25}$Si$_4$Na$^+$, 2058.84; found 2058.88 [M+Na]$^−$ 5-O-[Dodecyl-(Boc)$_3$-cyclam]-1,3,2',6',3''-penta-N-Boc-4',2'',4'',6''-tetra-O-TBDMS-tobramycin (16c). $^1$H NMR (300 MHz, CDCl$_3$) δ 5.28-5.10 (m, 2H, anomeric), 3.85-3.04 (m, 25H), 2.59-2.25 (m, 6H), 1.99-1.78 (m, 3H), 1.73-1.55 (m, 4H), 1.45-1.34 (m, 55H), 1.28-1.12 (m, 20H), 0.93-0.71 (m, 36H, TBDMS tert-butyl), 0.18-0.09 (m, 24H, TBDMS-CH$_3$). $^{13}$C NMR (75 MHz, CDCl$_3$) δ 155.68, 155.53, 154.81, 154.56, 96.46, 91.67, 85.72, 79.89, 79.53, 79.35, 79.19, 75.25, 73.33, 72.68, 71.53, 68.05, 66.83, 63.09, 60.32, 57.26, 55.48, 50.53, 48.36, 46.97, 45.67, 36.66, 35.61, 30.64, 30.06, 29.77, 29.71, 29.68, 28.62, 28.47, 28.38, 27.69, 26.22, 26.11, 26.00, 25.97, 25.76, 24.69, 23.54, 20.97, 18.46, 18.30, 18.08, 17.89, 14.15, 7.93, −3.46, −3.81, −4.22, −4.91, −4.96, −5.09, −5.19, −5.26. MALDI TOF-MS m/e calcd for C$_{104}$H$_{203}$N$_9$O$_9$Si$_4$Na$^+$, 2113.386; measured m/e, 2113.381 [M+Na]$^+$.

Microbiology. Bacteria isolates were either obtained from the American Type Culture Collection (ATCC), the Canadian National Intensive Care Unit (CAN-ICU) surveillance study (38), or the Canadian Ward (CANWARD) surveillance study (36, 37). Clinical isolates obtained as part of the CAN-ICU and CANWARD studies from participating medical centers across Canada were cultured from body fluids and tissues of patients suffering from presumed "clinically significant" infectious diseases. Antimicrobial susceptibilities of clinical isolates were evaluated (using ATCC strains as quality control strains) and categorized, where appropriate, as either multidrug resistant (MDR), extensively drug-resistant (XDR), or pan drug-resistant (PDR). MDR is defined as acquired non-susceptibility to at least one agent in three or more antimicrobial categories, XDR as non-susceptibility to at least one agent in all but two or fewer antimicrobial categories (i.e. bacterial isolates remain susceptible to only one or two categories), and PDR as non-susceptibility to all agents in all antimicrobial categories.[5]

Antimicrobial Susceptibility Assay. The in vitro antimicrobial activity of all compounds/antibiotics against a panel of bacteria was evaluated by microbroth dilution method in accordance with the Clinical and Laboratory Standards Institute (CLSI) guidelines. Overnight grown bacterial cultures were diluted in saline to achieve a 0.5 McFarland turbidity, followed by 1:50 dilution in Mueller-Hinton broth (MHB) for inoculation to a final concentration of approximately 5×10$^5$ CFU/mL. The antimicrobial agents were 2-fold serially diluted in MHB in a 96-well plate and incubated at 37° C. with equal volumes of inoculum for 18 h. The lowest concentration that prevented the visible growth of bacteria was defined as the MIC for each antimicrobial agent. The broth with or without bacterial cells was used as positive or negative control, respectively.

Checkerboard Assay. Combination studies with different antibiotics were performed in 96-well plates as previously described (22). Briefly, the antibiotic of interest was serially diluted in MHB along the abscissa while the adjuvant (newly synthesized conjugates) was serially diluted in MHB along the ordinate. This creates a 10×7 matrix wherein each well consists of a combination of different antibiotic and adjuvant concentrations. Overnight grown bacterial cultures were diluted in saline to achieve a 0.5 McFarland turbidity, followed by 1:50 dilution in Mueller-Hinton broth (MHB) for inoculation to a final concentration of approximately $5 \times 10^5$ CFU/mL. Equal volume of this bacterial culture was then added to each well and incubated at 37° C. for 18 h. After incubation, the plates were read on EMax® Plus microplate reader (Molecular Devices, Sunnyvale, CA, USA) at 590 nm. MIC was recorded as wells with the lowest concentration of drugs with no bacterial growth. The fractional inhibitory concentration (FIC) for each antibiotic was calculated by dividing the MIC of the antibiotic in the presence of adjuvant by the MIC of the antibiotic alone. Similarly, the FIC of adjuvant was calculated by dividing the MIC of the adjuvant in the presence of antibiotic by the MIC of the adjuvant alone. FIC index is the sum of both FICs. FIC indices of <0.5 were deemed synergistic; 0.5-4, no interaction; and >4, antagonistic.

Time-kill assay. Time-kill curve analyses were performed by culturing *P. aeruginosa* in LB medium, in the presence of antibiotics alone and in combination with test adjuvants. MICs of antibiotics and adjuvants were determined before the experiment following CLSI microbroth dilution guidelines. Growth curves were initially performed to confirm that all strains will reach a stable early- to mid-log phase after 4 h of pre-incubation in antimicrobial-free LB medium. A 0.5 McFarland inoculum of each strain was prepared in sterile 0.85% saline solution from an overnight grown culture. For each strain, 30 µl of the prepared inoculum was diluted to 3 ml of LB broth (containing different combinations of antimicrobial agents and adjuvants) and incubated at 37° C. shaking at 250 rpm. At specific time intervals (0, 1, 3, 6, 9, and 24 h), 100 µl was taken from each sample, serially diluted in sterile PBS, plated on LB agar plates, and incubated at 37° C. in a humid 5% $CO_2$-enriched atmosphere. Bacteria colonies were counted after 20 h of incubation.

In vivo larvae-infection model. In vivo synergistic effects were determined using *Galleria mellonella* infection model, as previously described (20). Briefly, worms were purchased from The Worm Lady® Live Feeder (ON, Canada), stored in their natural habitat at 16° C., and used within 10 days of delivery. The worms (average weight of 250 mg) were used for tolerability and efficacy studies. Tolerability study was performed by injecting 10 µL of antimicrobial agents only at concentrations equivalent to 100 mg/kg or 200 mg/kg. The worms (ten in each group) were incubated at 37° C. and monitored for 96 h. For efficacy studies, the virulence and bacterial load required to kill 100% of the worms within 12-18 h (with no treatment) was first determined, which is approximately 5 CFU. Overnight grown culture of respective MDR *P. aeruginosa* isolate was standardized to 0.5 McFarland standard and diluted in PBS to a final concentration of $5 \times 10^2$ CFU/mL. 10 µL of this solution (5 CFU) was injected into each worm and incubated for 3 h at 37° C. After the 3 h challenge, worms in monotherapy experimental groups (fifteen worms per group) were treated with 10 µL injection of aztreonam, meropenem, ceftazidime, avibactam, compound 2, or PBS alone. The worms in combination therapy groups were treated with aztreonam+compound 2 (12.5+12.5 mg/kg or 25+25 mg/kg), meropenem+compound 2 (25+25 mg/kg or 37.5+37.5 mg/kg), ceftazidime+avibactam (1.56+1.56 mg/kg), or ceftazidime+avibactam+compound 2 (1.56+1.56+3.12 mg/kg). Worms treated with 10 µL PBS or high concentrations of test antibiotics served as negative and positive control, respectively. The worms were incubated at 37° C. in Petri dishes lined with filter paper and scored for survivability every 6 h for up to 48 h. This experiment was repeated to give a total of thirty worms (n=30) in each case. Survival data curves were plotted using Kaplan-Meier survival analysis. Worms were considered dead if they do not respond to touch.

Cytotoxicity Assay. Human embryonic kidney cells (HEK293) and HepG2 cells were grown in Dulbecco's modified eagle's medium supplemented with 10% fetal bovine serum in a humidified 5% atmospheric incubator at 37° C. Equal number of cells (100 µl of media containing ~8000 cells) were dispersed into 96-well plates and wells with medium but no cells were used as blanks. After incubating for 24 h, 100 µl of varying concentrations of test compounds (at twice the desired concentrations) were added to each well, including the blanks. The treated cells were then incubated further for 48 h, after which PrestoBlue reagent was added to each well. The plates were then incubated for an additional hour on a nutator mixer in a 5% $CO_2$ incubator. The fluorescence was read at 490 nm on a SpectraMax M2 plate reader (Molecular Devices, USA). Cell viability were interpreted as previously described (55, 77). The values of blank were subtracted from each value, and the viability values of the treated samples relative to the controls with vehicle were calculated. The values for the plots are the means±standard deviation.

Hemolytic Assay. The hemolytic activities of the newly synthesized compounds were determined and quantified as the amount of hemoglobin released by lysing porcine erythrocytes. Fresh blood drawn from the antecubital vein of a pig (Animal Care and Use Program, University of Manitoba) was centrifuged at 1000 g at 4° C. for 10 mins, washed with PBS thrice and resuspended in the same buffer. The final cell concentration used was $3 \times 10^8$ cells/mL. Compounds were serially diluted with PBS and added to wells in a 96-well plate at twice the desired concentrations. Equal volumes of erythrocyte solution were then added to each well and incubated at 37° C. for 1 h. Intact erythrocytes were subsequently pelleted by centrifuging at 1000 g at 4° C. for 10 mins, and the supernatants were transferred to a new 96-well plate. Hemoglobin release was determined by measuring the absorbance on EMax® Plus microplate reader (Molecular Devices, Sunnyvale, CA, USA) at 570 nm. Blood cells in PBS (0% hemolysis) and 0.1% Triton X-100 (100% hemolysis) were used as negative and positive controls, respectively. Percent hemolysis was calculated as [% hemolysis= (X−0%)/(100%−0%)], where X is the optical density values of the compounds at different concentrations.

While the preferred embodiments of the invention have been described above, it will be recognized and understood that various modifications may be made therein, and the appended claims are intended to cover all such modifications which may fall within the spirit and scope of the invention.

REFERENCES (1) www.who.int/news-room/detail/27-02-2017-who-publishes-list-of-bacteria-for-which-new-antibiotics-are-urgently-needed (accessed Nov. 12, 2018).

(2) www.cdc.gov/drugresistance/threat-report-2013/(accessed Nov. 12, 2018).

(3) Tzouvelekis, L. S.; Markogiannakis, A.; Psichogiou, M.; Tassios, P. T.; Daikos, G. L. Carbapenemases in *Klebsiella pneumoniae* and Other Enterobacteriaceae: An Evolving Crisis of Global Dimensions. *Clin. Microbiol. Rev.* 2012, 25 (4), 682-707.

(4) Zavascki, A. P.; Bulitta, J. B.; Landersdorfer, C. B. Combination Therapy for Carbapenem-Resistant Gram-Negative Bacteria. *Expert Rev. Anti. Infect. Ther.* 2013, 11 (12), 1333-1353.

(5) Magiorakos, A. P.; Srinivasan, A.; Carey, R. B.; Carmeli, Y.; Falagas, M. E.; Giske, C. G.; Harbarth, S.; Hindler, J. F.; Kahlmeter, G.; Olsson-Liljequist, B.; Paterson, D. L.; Rice, L. B.; Stelling, J.; Struelens, M. J.; Vatopoulus, A.; Weber, J. T.; Monnet, D. L. Multidrug-Resistant, Extensively Drug-Resistant and Pandrug-Resistant Bacteria: An International Expert Proposal for Interim Standard Definitions for Acquired Resistance. *Clin. Microbiol. Infect.* 2012, 18 (3), 268-281.

(6) Delcour, A. H. Outer Membrane Permeability and Antibiotic Resistance. *Biochim. Biophys. Acta* 2009, 1794 (5), 808-816.

(7) Stover, C. K.; Pham, X. Q.; Erwin, A. L.; Mizoguchi, S. D.; Warrener, P.; Hickey, M. J.; Brinkman, F. S.; Hufnagle, W. O.; Kowalik, D. J.; Lagrou, M.; Garber, R. L.; Goltry, L.; Tolentino, E.; Westbrock-Wadman, S.; Yuan, Y.; Brody, L. L; Coulter, S. N.; Folger, K. R.; Kas, A.; Larbig, K.; Lim, R.; Smith, K.; Spencer, D.; Wong, G. K.; Wu, Z.; Paulsen, I. T.; Reizer, J.; Saier, M. H.; Hancock, R. E.; Lory, S.; Olson, M. V. Complete Genome Sequence of *Pseudomonas aeruginosa* PAO1, an Opportunistic Pathogen. *Nature* 2000, 406 (6799), 959-964.

(8) Hancock, R. E. W.; Brinkman, F. S. L. Function of *Pseudomonas* Porins in Uptake and Efflux. *Annu. Rev. Microbiol* 2002, 56, 17-38.

(9) Nikaido, H. Molecular Basis of Bacterial Outer Membrane Permeability Revisited. *Microbiol. Mol. Biol. Rev.* 2003, 67 (4), 593-656.

(10) Li, X.-Z.; Plésiat, P.; Nikaido, H. The Challenge of Efflux-Mediated Antibiotic Resistance in Gram-Negative Bacteria. *Clin. Microbiol. Rev.* 2015, 28 (2), 337-418.

(11) Breidenstein, E. B. M.; de la Fuente-Núñez, C.; Hancock, R. E. W. *Pseudomonas aeruginosa*: All Roads Lead to Resistance. *Trends Microbiol.* 2011, 19 (8), 419-426.

(12) Strateva, T.; Yordanov, D. *Pseudomonas aeruginosa*—a Phenomenon of Bacterial Resistance. *J. Med. Microbiol.* 2009, 58 (Pt 9), 1133-1148.

(13) Domalaon, R.; Idowu, T.; Zhancl, G. G.; Schweizer, F. Antibiotic Hybrids: The Next Generation of Agents and Adjuvants against Gram-Negative Pathogens? *Clin. Microbiol. Rev.* 2018, 31 (2), e00077-17.

(14) Richter, M. F.; Drown, B. S.; Riley, A. P.; Garcia, A.; Shirai, T.; Svec, R. L.; Hergenrother, P. J. Predictive Compound Accumulation Rules Yield a Broad-Spectrum Antibiotic. *Nature* 2017, 545, 299-304.

(15) Idowu, T.; Schweizer, F. Ubiquitous Nature of Fluoroquinolones: The Oscillation between Antibacterial and Anticancer Activities. *Antibiotics* 2017, 6 (4), 26.

(16) Hancock, R. E. Aminoglycoside Uptake and Mode of Action—with Special Reference to Streptomycin and Gentamicin. I. Antagonists and Mutants. *J. Antimicrob. Chemother.* 1981, 8 (4), 249-276.

(17) Bulitta, J. B.; Ly, N. S.; Landersdorfer, C. B.; Wanigaratne, N. A.; Velkov, T.; Yadav, R.; Oliver, A.; Martin, L.; Shin, B. S.; Forrest, A.; Tsuji, B. T. Two Mechanisms of Killing of *Pseudomonas aeruginosa* by Tobramycin Assessed at Multiple Inocula via Mechanism-Based Modeling. *Antimicrob. Agents Chemother.* 2015, 59 (4), 2315-2327.

(18) Shakil, S.; Khan, R.; Zarrilli, R.; Khan, A. U. Aminoglycosides versus Bacteria—a Description of the Action, Resistance Mechanism, and Nosocomial Battleground. *J. Biomed. Sci.* 2008, 15 (1), 5-14,

(19) Garneau-Tsodikova, S.; Labby, K. J. Mechanisms of Resistance to Aminoglycoside Antibiotics: Overview and Perspectives. *Med. Chem. Commun.* 2016, 7 (1), 11-27.

(20) Gorityala, B. K.; Guchhait, G.; Fernando, D. M.; Deo, S.; McKenna, S. A.; Zhanel, G. G.; Kumar, A.; Schweizer, F. Adjuvants Based on Hybrid Antibiotics Overcome Resistance in *Pseudomonas aeruginosa* and Enhance Fluoroquinolone Efficacy. *Angew. Chem. Int. Ed. Engl.* 2016, 55 (2), 555-559.

(21) Herzog, I. M.; Green, K. D.; Berkov-Zrihen, Y.; Feldman, M.; Vidayski, R. R.; Eldar-Boock, A.; Satchi-Fainaro, R.; Eldar, A.; Garneau-Tsodikova, S.; Fridman, M. 6"-Thioether Tobramycin Analogues: Towards Selective Targeting of Bacterial Membranes. *Angew. Chemie— Int. Ed.* 2012, 51 (23), 5652-5656.

(22) Lyu, Y.; Yang, X.; Goswami, S.; Gorityala, B. K.; Idowu, T.; Domalaon, R.; Zhanel, G. G.; Shan, A.; Schweizer, F. Amphiphilic Tobramycin-lysine Conjugates Sensitize Multidrug Resistant Gram-Negative Bacteria to Rifampicin and Minocycline. *J. Med. Chem.* 2017, 60 (9), 3684-3702.

(23) Gorityala, B. K.; Guchhait, G.; Goswami, S.; Fernando, D. M.; Kumar, A.; Zhanel, G. G.; Schweizer, F. Hybrid Antibiotic Overcomes Resistance in *P. aeruginosa* by Enhancing Outer Membrane Penetration and Reducing Efflux. *J Med. Chem.* 2016, 59 (18), 8441-8455.

(24) Drawz, S. M.; Bonomo, R. A. Three Decades of β-Lactamase Inhibitors. *Clin. Microbial. Rev.* 2010, 23 (1), 160-201.

(25) Li, H.; Luo, Y.-F.; Williams, B. J.; Blackwell, T. S.; Xie, C.-M. Structure and Function of OprD Protein in *Pseudomonas aeruginosa*: From Antibiotic Resistance to Novel Therapies. *Int. J. Med. Microbial.* 2011, 302, 63-68.

(26) Quale, J.; Bratu, S.; Gupta, J.; Landman, D. Interplay of Efflux System, AmpC, and OprD Expression in Carbapenem Resistance of *Pseudomonas aeruginosa* Clinical Isolates. *Antimicrob. Agents Chemother.* 2006, 50 (5), 1633-1641.

(27) Conejo, M. C.; Garcia, I.; Martinez-Martinez, L.; Picabea, L.; Pascual, A. Zinc Eluted from Siliconized Latex Urinary Catheters Decreases OprD Expression, Causing Carbapenem Resistance in *Pseudomonas aeruginosa*. *Antimicrob. Agents Chemother.* 2003, 47 (7), 2313-2315.

(28) Perron, K.; Caille, O.; Rossier, C.; van Delden, C.; Dumas, J.-L.; Köhler, T. CzcR-CzcS, a Two-Component System Involved in Heavy Metal and Carbapenem Resistance in *Pseudomonas aeruginosa*. *J. Biol. Chem.* 2004, 279 (10), 8761-8768. (29) Caille, O.; Rossier, C.; Perron, K. A Copper-Activated Two-Component System Interacts with Zinc and Imipenem Resistance in *Pseudomonas aeruginosa*. *J. Bacteria* 2007, 189 (13), 4561-4568.

(30) Vaara, M. Agents That Increase the Permeability of the Outer Membrane. *Microbial. Rev.* 1992, 56 (3), 395-411.

(31) King, A. M.; Reid-Yu, S. a; Wang, W.; King, D. T.; De Pascale, G.; Strynadka, N. C.; Walsh, T. R.; Coombes, B. K.; Wright, G. D. Aspergillomarasmine A Overcomes Metallo-β-Lactamase Antibiotic Resistance. *Nature* 2014, 510 (7506), 503-506.

(32) Yu, M.; Nagalingam, G.; Ellis, S.; Martinez, E.; Sintchenko, V.; Spain, M.; Rutledge, P. J.; Todd, M. H.; Triccas, J. A. Nontoxic Metal-Cyclam Complexes, a New Class of Compounds with Potency against Drug-Resistant *Mycobacterium tuberculosis*. *J. Med. Chem.* 2016, 59 (12), 5917-5921.

(33) Liang, X.; Sadler, P. J. Cyclam Complexes and Their Applications in Medicine. *Chem. Soc. Rev.* 2004, 33 (4), 246.

(34) Allam, A.; Maigre, L.; Alves De Sousa, R.; Dumont, E.; Vergalli, J.; Pag Es, J.-M.; Artaud, I. New Amphiphilic Neamine Conjugates Bearing a Metal Binding Motif Active against MDR *E. aerogenes* Gram-Negative Bacteria. *Eur. J. Med Chem.* 2017, 127, 748-756.

(35) Guchhait, G.; Altieri, A.; Gorityala, B.; Yang, X.; Findlay, B.; Zhanel, G. G.; Mookherjee, N.; Schweizer, F. Amphiphilic Tobramycins with Immunomodulatory Properties. *Angew. Chem. Int. Ed. Engl.* 2015, 54 (21), 6278-6282.

(36) Zhanel, G. G.; Adam, H. J.; Baxter, M. R.; Fuller, J.; Nichol, K. A.; Denisuik, A. J.; Lagacé-Wiens, P. R. S.; Walkty, A.; Karlowsky, J. A.; Schweizer, F.; Hoban, D. J. Antimicrobial Susceptibility of 22746 Pathogens from Canadian Hospitals: Results of the CANWARD 2007-11 Study. *J. Antimicrob. Chemother.* 2013, 68 Suppl 1, i7-22.

(37) Zhanel, G. G.; DeCorby, M.; Adam, H.; Mulvey, M. R.; McCracken, M.; Lagace-Wiens, P.; Nichol, K. A.; Wierzbowski, A.; Baudry, P. J.; Tailor, F.; Karlowsky, J. A.; Walkty, A.; Schweizer, F.; Johnson, J.; Hoban, D. J. Prevalence of Antimicrobial-Resistant Pathogens in Canadian Hospitals: Results of the Canadian Ward Surveillance Study (CANWARD 2008). *Antimicrob. Agents Chemother.* 2010, 54 (11), 4684-4693.

(38) Zhanel, G. G.; DeCorby, M.; Laing, N.; Weshnoweski, B.; Vashisht, R.; Tailor, F.; Nichol, K. A.; Wierzbowski, A.; Baudry, P. J.; Karlowsky, J. A.; Lagace-Wiens, P.; Walkty, A.; McCracken, M.; Mulvey, M. R.; Johnson, J.; Hoban, D. J. Antimicrobial-Resistant Pathogens in Intensive Care Units in Canada: Results of the Canadian National Intensive Care Unit (CAN-ICU) Study, 2005-2006. *Antimicrob. Agents Chemother.* 2008, 52 (4), 1430-1437.

(39) Wright, G. D. Antibiotic Adjuvants: Rescuing Antibiotics from Resistance. *Trends Microbiol.* 2016, 24 (11), 862-871.

(40) Zhanel, G. G.; Lawson, C. D.; Zelenitsky, S.; Findlay, B.; Schweizer, F.; Adam, H.; Walkty, A.; Rubinstein, E.; Gin, A. S.; Hoban, D. J.; Lynch, J. P.; Karlowsky, J. A. Comparison of the Next-Generation Aminoglycoside Plazomicin to Gentamicin, Tobramycin and Amikacin. *Expert Rev. Anti. Infect. Ther.* 2012, 10 (4), 459-473.

(41) Pai, M. P.; Nafziger, A. N.; Bertino, J. S. Simplified Estimation of Aminoglycoside Pharmacokinetics in Underweight and Obese Adult Patients. *Antimicrob. Agents Chemother.* 2011, 55 (9), 4006-4011.

(42) MacNair, C. R.; Stokes, J. M.; Carfrae, L. A.; Fiebig-Comyn, A. A.; Coombes, B. K.; Mulvey, M. R.; Brown, E. D. Overcoming Mer-1 Mediated Colistin Resistance with Colistin in Combination with Other Antibiotics. *Nat. Commun.* 2018, 9 (1), 1-8.

(43) Pai, H.; Kim, J.; Kim, J.; Lee, J. H.; Choe, K. W.; Gotoh, N. Carbapenem Resistance Mechanisms in *Pseudomonas aeruginosa* Clinical Isolates. *Antimicrob. Agents Chemother.* 2001, 45 (2), 480-484.

(44) *CLSI. Performance Standards for Antimicrobial Susceptibility Testing.* 27th Ed. CLSI Supplement M100. Wayne, PA: Clinical and Laboratory Standards Institute; 2017.

(45) Poole, K.; Gilmour, C.; Farha, M. A.; Parkins, M. D.; Klinoski, R.; Brown, E. D. Meropenem Potentiation of Aminoglycoside Activity against *Pseudomonas aeruginosa*: Involvement of the MexXY-OprM Multidrug Efflux System. *J. Antimicrob. Chemother.* 2018, 73, 1247-1255.

(46) Lomovskaya, O.; Warren, M. S.; Lee, A.; Fronko, R.; Lcc, M.; Blais, J.; Chamberland, S.; Renau, T.; Leger, R.; Hecker, S.; et al. Identification and Characterization of Inhibitors of Multidrug Resistance Efflux Pumps in *Pseudomonas aeruginosa*: Novel Agents for Combination Therapy. *Antimicrob. Agents Chemother.* 2001, 45 (1), 105-116.

(47) Kumar, A.; Chua, K. L.; Schweizer, H. P. Method for Regulated Expression of Single-Copy Efflux Pump Genes in a Surrogate *Pseudomonas aeruginosa* Strain: Identification of the BpeEF-OprC Chloramphenicol and Trimethoprim Efflux Pump of *Burkholderia pseudomallei* 1026b. *Antimicrob. Agents Chemother.* 2006, 50 (10), 3460-3463.

(48) Masuda, N.; Sakagawa, E.; Ohya, S.; Gotoh, N.; Tsujimoto, H.; Nishino, T. Contribution of the MexX-MexY-OprM Efflux System to Intrinsic Resistance in *Pseudomonas aeruginosa*. *Antimicrob. Agents Chemother.* 2000, 44 (9), 2242-2246.

(49) Masuda, N.; Sakagawa, E.; Ohya, S.; Gotoh, N.; Tsujimoto, H.; Nishino, T. Substrate Specificities of MexAB-OprM, MexCD-OprJ, and MexXY-OprM Efflux Pumps in *Pseudomonas aeruginosa*. *Antimicrob. Agents Chemother.* 2000, 44 (12), 3322-3327.

(50) Lahiri, S. D.; Johnston; M. R.; Ross, P. L.; McLaughlin, R. E.; Olivier, N. B.; Alm, R. A. Avibactam and Class C β-Lactamases: Mechanism of Inhibition, Conservation of the Binding Pocket, and Implications for Resistance. *Antimicrob. Agents Chemother.* 2014, 58 (10), 5704-5713.

(51) King, D. T.; King, A. M.; Lal, S. M.; Wright, G. D.; Strynadka, N. C. J. Molecular Mechanism of Avibactam-Mediated β-Lactamase Inhibition. *ACS Infect, Dis.* 2015, 1 (4), 175-184.

(52) Pournaras, S.; Vrioni, G.; Neou, E.; Dendrinos, J.; Dimitroulia, E.; Poulou, A.; Tsakris, A. Activity of Tigecycline Alone and in Combination with Colistin and Meropenem against *Klebsiella pneumoniae* Carbapenemase (KPC)-Producing Enterobacteriaceae Strains by Time-Kill Assay. *Int. J. Antimicrob. Agents* 2011, 37 (3), 244-247.

(53) Krezdorn, J.; Adams, S.; Coote, P. J. A *Galleria mellonella* Infection Model Reveals Double and Triple Antibiotic Combination Therapies with Enhanced Efficacy versus a Multidrug-Resistant Strain of *Pseudomonas aeruginosa*. *J. Med. Microbiol* 2014, 63, 945-955.

(54) Hill, L; Veli, N.; Coote, P. J. Evaluation of *Galleria mellonella* Larvae for Measuring the Efficacy and Pharmacokinetics of Antibiotic Therapies against *Pseudomonas aeruginosa* Infection. *Int. J. Antimicrob. Agents* 2014, 43 (3), 254-261.

(55) Idowu, T.; Samadder, P.; Arthur, G.; Schweizer, F. M. Amphiphilic Modulation of Glycosylated Antitumor Ether Lipids Results in a Potent Triamino Scaffold against Epithelial Cancer Cell Lines and BT474 Cancer Stem Cells. *J. Med Chem.* 2017, 60, 9724-9738.

(56) Nordmann, P.; Naas, T.; Poirel, L. Global Spread of Carbapenemase Producing Enterobacteriaceae. *Emerg. Infect. Dis.* 2011, 17 (10), 1791-1798.

(57) Ouberai, M.; El Garch, F.; Bussiere, A.; Riou, M.; Alsteens, D.; Lins, L.; Baussanne, L; Dufrêne, Y. F.; Brasseur, R.; Décout, J.-L.; Mingeot-Leclereq, M.-P. The *Pseudomonas aeruginosa* Membranes: A Target for a New Amphiphilic Aminoglycoside Derivative? *Biochim. Biophys. Acta* 2011, 1808 (6), 1716-1727.

(58) Stokes, J. M.; Macnair, C. R.; Ilyas, B.; French, S.; Côte, J.-P.; Bouwman, C.; Farha, M. A.; Sieron, A. O.; Whitfield, C.; Coombes, B. K.; et al. Pentamidine Sensitizes Gram-Negative Pathogens to Antibiotics and Overcomes Acquired Colistin Resistance. *Nat. Microbiol.* 2017, 2, 17028.

(59) Corbett, D.; Wise, A.; Langley, T.; Skinner, K.; Trimby, E.; Birchall, S.; Dorali, A.; Sandiford, S.; Williams, J.; Warn, P.; Vaara, M.; Lister, T. Potentiation of Antibiotic Activity by a Novel Cationic Peptide: Potency and Spectrum of Activity of SPR741. *Antimicrob. Agents Chemother.* 2017, 61 (8), e00200-17.

(60) Ferrara, A.; Grassi, F. A.; Grassi, G.; Piccioni, P. D.; Grassi, G. G. Bactericidal Activity of Meropenem and Interactions with Other Antibiotics. *J. Antimicrob. Chemother.* 1989, 24 (suppl A), 239-250.

(61) Nakamura, A.; Hosoda, M.; Kato, T.; Yamada, Y.; Itoh, M.; Kanazawa, K.; Nouda, H. Combined Effects of Meropenem and Aminoglycosides on *Pseudomonas aeruginosa* in Vitro. *J. Antimicrob. Chemother.* 2000, 46 (6), 901-904.

(62) Queenan, A. M.; Bush, K. Carbapenemases: The Versatile β-Lactamases. *Clin. Microbiol. Rev.* 2007, 20 (3), 440-458.

(63) Hurdle, J. G.; O'Neill, A. J.; Lee, R. E. Targeting Bacterial Membrane Function: An Underexploited Mechanism for Treating Persistent Infections. *Nat. Rev. Microbiol.* 2011, 9 (1), 62-75.

(64) Kulengowski, B.; Campion, J. J.; Feola, D. J.; Burgess, D. S. Effect of the Meropenem MIC on the Killing Activity of Meropenem and Polymyxin B in Combination against KPC-Producing *Klebsiella pneumoniae*. *J. Antibiot.* (Tokyo). 2017, 70, 974-978.

(65) El-Halfawy, O. M.; Valvano, M. A. Antimicrobial Heteroresistance: An Emerging Field in Need of Clarity. *Clin. Microbiol. Rev.* 2015, 28 (1), 191-207.

(66) Sabet, M.; Tarazi, Z.; Nolan, T.; Parkinson, J.; Rubio-Aparicio, D.; Lomovskaya, O.; Dudley, M. N.; Griffith, D. C. Activity of Meropenem-Vaborbactam in Mouse Models of Infection Due to KPC-Producing Carbapenem-Resistant Enterobacteriaceae. *Antimicrob. Agents Chemother.* 2017, 62 (1), e01446-17.

(67) Tamma, P. D.; Cosgrove, S. E.; Maragakis, L. L. Combination Therapy for Treatment of Infections with Gram-Negative Bacteria. *Clin. Microbiol. Rev.* 2012, 25 (3), 450-470.

(68) Safdar, N.; Handelsman, J.; Maki, D. G. Does Combination Antimicrobial Therapy Reduce Mortality in Gram Negative Bacteraemia? A Meta-Analysis. *Lancet Infect. Dis.* 2004, 4 (8), 519-527.

(69) Paul, M.; Lador, A.; Grozinsky-Glasberg, S.; Leibovici, L. Beta Lactam Antibiotic Monotherapy versus Beta Lactam-Aminoglycoside Antibiotic Combination Therapy for Sepsis. *Cochrane Database Syst. Rev.* 2014, 1, CD003344.

(70) Yaneja, N.; Kaur, H. Insights into Newer Antimicrobial Agents against Gram-Negative Bacteria. *Microbiol. Insights* 2016, 9, 9-19.

(71) Butler, M. S.; Blaskovich, M. A.; Cooper, M. A. Antibiotics in the Clinical Pipeline at the End of 2015. *J. Antibiot.* (Tokyo). 2017, 70 (1), 3-24.

(72) Zhanel, G. G.; Chung, P.; Adam, H.; Zelenitsky, S.; Denisuik, A.; Schweizer, F.; Lagacé-Wiens, P. R. S.; Rubinstein, E.; Gin, A. S.; Walkty, A.; Hoban, D. J.; Lynch, J. P.; Karlowsky, J. A. Ceftolozane/Tazobactam: A Novel Cephalosporin/β-Lactamase Inhibitor Combination with Activity Against Multidrug-Resistant Gram-Negative Bacilli. *Drugs* 2014, 74 (1), 31-51.

(73) Cabot, G.; Bruchmann, S.; Mulet, X.; Zamorano, L.; Moyà, B.; Juan, C.; Haussler, S.; Oliver, A. *Pseudomonas aeruginosa* Ceftolozane-Tazobactam Resistance Development Requires Multiple Mutations Leading to Overexpression and Structural Modification of AmpC. *Antimicrob. Agents Chemother.* 2014, 58 (6), 3091-3099.

(74) Efficacy and Safety of Imipenem+Cilastatin/Relebactam (MK-7655A) Versus Colistimethate Sodium+Imipenem+Cilastatin in Imipenem-Resistant Bacterial infection clinicaltrials.gov/ct2/show/results/NCT02452047 (accessed Oct. 29, 2018).

(75) Entasis Therapeutics entasistx.gcs-web.com (accessed Aug. 23, 2018).

(76) Kitagawa, T.; Dey, A.; Lugo-Mas, P.; Benedict, J. B.; Kaminsky, W.; Solomon, E.; Kovacs, J. A. A Functional Model for the Cysteinate-Ligated Non-Heme Iron Enzyme Superoxide Reductase (SOR). *J. Am. Chem. Soc.* 2006, 128 (45), 14448-14449.

(77) Idowu, T.; Samadder, P.; Arthur, G.; Schweizer, F. Design, Synthesis and Antitumor Properties of Glycosylated Antitumor Ether Lipid (GAEL)-Chlorambucil-Hybrids. *Chem. Phys. Lipids* 2016, 194, 139-148.

TABLE 1

Minimum inhibitory concentrations (MICs, μg/ml) of Tobramycin and compounds 1-3 against a panel of Gram-positive and Gram-negative bacteria

| Test organism | Tobramycin | TOBRAMYCIN-CYCLAM CONJUGATES | | |
|---|---|---|---|---|
| | | 1 | 2 | 3 |
| S. aureus ATCC 29213 | 0.5 | 64 | 128 | >128 |
| MRSA ATCC 33592 | 0.5 | 64 | 64 | >128 |
| MSSE CANWARD-2008 81388 | ≤0.25 | 16 | 16 | 16 |
| MRSE CAN-ICU 61589 (CAZ >32) | 2 | 64 | 128 | 32 |
| E. faecalis ATCC 29212 | 8 | >128 | >128 | >128 |
| E. faecium ATCC 27270 | 16 | >128 | >128 | >128 |
| S. pneumoniae ATCC 49619 | 2 | >128 | >128 | >128 |
| E. coli ATCC 25922 | 0.5 | 64 | 64 | 64 |
| E. coli CAN-ICU 61714 (GEN-R) | 8 | 128 | 128 | >128 |
| E. coli CAN-ICU 63074 (AMK 32) | 8 | >128 | >128 | >128 |
| E. coli CANWARD-2011 97615 (GEN-R, TOB-R, CIP-R) aac(3')iia | 128 | >128 | >128 | >128 |
| P. aeruginosa ATCC 27853 | 1 | >128 | >128 | >128 |
| P. aeruginosa CAN-ICU 62308 (GEN-R) | 16 | >128 | >128 | >128 |
| P. aeruginosa CANWARD-2011 96846 (GEN-R, TOB-R) | 256 | >128 | >128 | >128 |
| S. maltophilia CAN-ICU 62584 | >512 | >128 | >128 | >128 |
| A. baumannii CAN-ICU 63169 | 32 | >128 | >128 | >128 |
| K. pneumoniae ATCC 13883 | ≤0.25 | 32 | 128 | 64 |

TABLE 2

Combination studies of compounds 1-3 with different antibiotics against WT P. aeruginosa PAO1. MICs are reported in μg/ml.

| Antibiotics (MIC alone) | MIC of Antibiotics (FICI) in the presence of ≤ 10 μM of | | |
|---|---|---|---|
| | 1 | 2 | 3 |
| Rifampicin (16) | 2 (0.13) | 2 (0.13) | 4 (0.25) |
| Tobramycin (1) | 1 (1.01) | 1 (1.00) | 1 (1.01) |
| Minocycline (8) | 2 (0.25) | 2 (0.25) | 1 (0.17) |
| Cefotaxime (16) | 2 (0.13) | 4 (0.26) | 4 (0.27) |
| Doxycycline (8) | 4 (0.50) | 1 (0.13) | 0.5 (0.08) |
| Linezolid (1024) | 1024 (1.00) | 256 (0.26) | 256 (0.25) |
| Meropenem (1) | 0.25 (0.25) | 0.25 (0.26) | 0.5 (0.50) |
| Doripenem (1) | 0.5 (0.51) | 0.5 (0.50) | 0.5 (0.50) |
| Moxifloxacin (1) | 1 (1.00) | 0.5 (0.51) | 1 (1.01) |
| Trimethoprim (64) | 32 (0.50) | 32 (0.50) | 32 (0.50) |
| Vancomycin (256) | 128 (0.50) | 64 (0.26) | 128 (0.50) |
| Aztreonam (4) | 0.5 (0.13) | 0.25 (0.07) | 0.5 (0.14) |
| Ceftazidime (2) | 0.5 (0.25) | 0.25 (0.13) | 0.5 (0.25) |
| Fosfomycin (16) | 8 (0.51) | 8 (0.50) | 16 (1.02) |
| Nitrofurantoin (1024) | 1024 (1.00) | 1024 (1.00) | 1024 (1.02) |
| Chloramphenicol (32) | 8 (0.25) | 4 (0.13) | 8 (0.25) |
| Clindamycin (1024) | 512 (0.50) | 512 (0.51) | 64 (0.07) |
| Erythromycin (512) | 256 (0.50) | 256 (0.50) | 128 (0.25) |
| Pleuromutilin (512) | 512 (1.00) | 512 (1.00) | 128 (0.25) |
| Novobiocin (512) | 64 (0.13) | 64 (0.13) | 32 (0.08) |
| Colistin (1) | 2 (2.00) | 2 (2.00) | 1 (1.02) |
| Tigecycline (4) | 2 (0.25) | 2 (0.50) | 2 (0.52) |
| Piperacillin (8) | 2 (0.26) | 2 (0.25) | 2 (0.25) |

FICI = Fractional inhibitory concentration index. FICI of < 0.5, 0.5-4, and > 4 indicate synergy, additive or no interaction, and antagonism, respectively. Synergistic combinations are underlined.

TABLE 3

| Strain | Antibiotic | MIC$_{Antibiotic}$ | MIC$_{Combination}$ | FIC$_{Antibiotic}$ | MIC$_2$ | MIC$_{Combination}$ | FIC$_2$ | FICl |
|---|---|---|---|---|---|---|---|---|
| PA 100036 | AZT | 16 | 2 | 0.125 | >256 | 8 | <0.0313 | <0.16 |
| | CAZ | 8 | 2 | 0.250 | >256 | 8 | <0.0313 | <0.28 |
| | PIP | 64 | 64 | 1.000 | >256 | 16 | <0.0625 | <1.06 |
| | MER | 4 | 2 | 0.500 | >256 | 2 | <0.0078 | <0.51 |
| | DOR | 16 | 8 | 0.500 | >256 | 16 | <0.0625 | <0.56 |
| | CEF | 32 | 8 | 0.250 | >256 | 16 | <0.0625 | <0.31 |
| PA 101885 | AZT | 16 | 0.5 | 0.031 | >256 | 16 | <0.0625 | <0.09 |
| | CAZ | 8 | 1 | 0.125 | >256 | 8 | <0.0313 | <0.16 |
| | PIP | 16 | 4 | 0.250 | >256 | 16 | <0.0625 | <0.31 |
| | MER | 4 | 0.5 | 0.125 | >256 | 8 | <0.0313 | <0.16 |
| | DOR | 4 | 1 | 0.250 | >256 | 4 | <0.0156 | <0.27 |
| | CEF | 128 | 8 | 0.063 | >256 | 16 | <0.0625 | <0.13 |
| PA 259 | AZT | 32 | 4 | 0.125 | >256 | 16 | <0.0625 | <0.19 |
| | CAZ | 512 | 64 | 0.125 | ≥256 | 16 | <0.0625 | ≤0.19 |
| | PIP | 512 | 256 | 0.500 | >256 | 1 | <0.0039 | <0.50 |
| | MER | 1024 | 256 | 0.250 | >256 | 16 | <0.0625 | <0.31 |
| | DOR | >1024 | ND | ND | >256 | ND | ND | ND |
| | CEF | 2048 | 512 | 0.250 | >256 | 16 | ≤0.0625 | <0.31 |
| PA 260 | AZT | 64 | 8 | 0.125 | >256 | 16 | <0.0625 | <0.19 |
| | CAZ | 32 | 16 | 0.500 | >256 | 4 | <0.0156 | <0.52 |
| | PIP | 512 | 512 | 1.000 | >256 | 16 | <0.0625 | <1.06 |
| | MER | 8 | 1 | 0.125 | >256 | 8 | <0.0313 | <0.16 |
| | DOR | 16 | 8 | 0.500 | >256 | 8 | <0.0313 | <0.53 |
| | CEF | 1024 | 512 | 0.500 | >256 | 8 | <0.0313 | <0.53 |
| PA 262 | AZT | 32 | 8 | 0.250 | >256 | 8 | <0.0313 | <0.28 |
| | CAZ | 16 | 4 | 0.250 | >256 | 16 | <0.0625 | <0.31 |
| | PIP | 1024 | 512 | 0.500 | >256 | 4 | <0.0156 | <0.52 |
| | MER | 32 | 2 | 0.063 | >256 | 16 | <0.0625 | <0.13 |
| | DOR | 16 | 4 | 0.250 | >256 | 16 | <0.0625 | <0.31 |
| | CEF | 128 | 32 | 0.250 | >256 | 16 | <0.0625 | <0.31 |
| PA 264 | AZT | 64 | 16 | 0.250 | >256 | 8 | <0.0313 | <0.28 |
| | CAZ | 128 | 32 | 0.250 | >256 | 8 | <0.0313 | <0.28 |
| | PIP | 2048 | 1024 | 0.500 | >256 | 4 | <0.0156 | <0.52 |
| | MER | 64 | 2 | 0.0313 | >256 | 4 | <0.0156 | <0.05 |
| | DOR | 16 | 8 | 0.500 | >256 | 4 | <0.0156 | <0.51 |
| | CEF | 2048 | 512 | 0.250 | >256 | 16 | <0.0625 | <0.31 |

TABLE 3-continued

| Strain | Antibiotic | MIC$_{Antibiotic}$ | MIC$_{Combination}$ | FIC$_{Antibiotic}$ | MIC$_2$ | MIC$_{Combination}$ | FIC$_2$ | FICI |
|---|---|---|---|---|---|---|---|---|
| PA 91433 | AZT | 512 | 512 | 1.000 | >256 | 16 | <0.0625 | <1.06 |
| | CAZ | 1024 | 512 | 0.500 | >256 | 0.25 | <0.0010 | <0.50 |
| | PIP | ND | ND | ND | >256 | ND | ND | NO |
| | MER | 16 | 0.25 | 0.016 | >256 | 4 | <0.0156 | <0.03 |
| | DOR | 16 | 1 | 0.063 | >256 | 8 | <0.0313 | <0.09 |
| | CEF | 1024 | 8 | 0.008 | >256 | 16 | <0.0625 | <0.07 |
| PA 101243 | AZT | 32 | 8 | 0.250 | >256 | 2 | <0.0078 | <0.26 |
| | CAZ | 64 | 8 | 0.125 | >256 | 1 | <0.0039 | <0.13 |
| | PIP | 128 | 128 | 1.000 | >256 | 16 | <0.0625 | <1.06 |
| | MER | 8 | 2 | 0.250 | >256 | 0.5 | ≤0.0020 | <0.25 |
| | DOR | 16 | 8 | 0.500 | >256 | 0.25 | <0.0010 | <0.50 |
| | CEF | 256 | 128 | 0.500 | >256 | 0.25 | <0.0010 | <0.50 |
| PA 114228 | AZT | 32 | 4 | 0.125 | >256 | 4 | <0.0156 | <0.14 |
| | CAZ | 8 | 1 | 0.125 | >256 | 16 | <0.0625 | <0.19 |
| | PIP | 16 | 8 | 0.500 | >256 | 0.5 | <0.0020 | <0.50 |
| | MER | 8 | 2 | 0.250 | >256 | 8 | <0.0313 | <0.28 |
| | DOR | 8 | 1 | 0.125 | >256 | 4 | <0.0156 | <0.14 |
| | CEF | 128 | 16 | 0.125 | >256 | 4 | <0.0156 | <0.14 |

Synergistic effects of compound 2 with aztreonam (AZT), ceftazidime (CAZ), piperacillin (PIP), meropenem (MER), doripenem (DOR), and cefotaxime (CEF) against multidrug resistant, extensively drug-resistant, and pan drug-resistant *P. aeruginosa* clinical isolates.
MICs are reported in µg/ml. FICI of <0.5, 0.5-2, and >2 indicate synergy, additive or no interaction, and antagonism, respectively.
ND = not determined.
Synergistic combinations are underlined.

TABLE 4

| | MIC of antibiotic alone in | | | MIC of antibiotic (fold change) + Compound 2 in | | |
|---|---|---|---|---|---|---|
| Antibiotics | PAO1 | PAO200 | PAO750 | PAO1 | PAO200 | PAO750 |
| Aztreonam | 4 | 0.25 | 0.5 | 0.25 (16) | 0.016 (16) | 0.031 (16) |
| Ceftazidime | 4 | 2 | 1 | 0.5 (8) | 0.125 (16) | 0.125 (8) |
| Piperacillin | 8 | 1 | 2 | 2 (4) | 1 (1) | 0.5 (4) |
| Meropenem | 1 | 0.25 | 1 | 0.25 (4) | 0.063 (4) | 0.25 (4) |
| Doripenem | 1 | 1 | 1 | 0.5 (2) | 0.25 (4) | 0.25 (4) |
| Cefotaxime | 16 | 8 | 32 | 4 (4) | 4 (2) | 2 (16) |

Potentiation of B-lactam antibiotics in *P. aeruginosa* by compound 2 (≤8.7 µM) is independent of RND efflux pumps. PAO1 = wild-type, PAO200 and PAO750 are efflux-deficient mutants. MICs are reported in µg/ml. Synergistic combinations are underlined.

The invention claimed is:

1. A compound comprising a chemical structure or chemical formula of Formula (A):

2. The compound according to claim 1 comprising a chemical structure or chemical formula of formula (I)

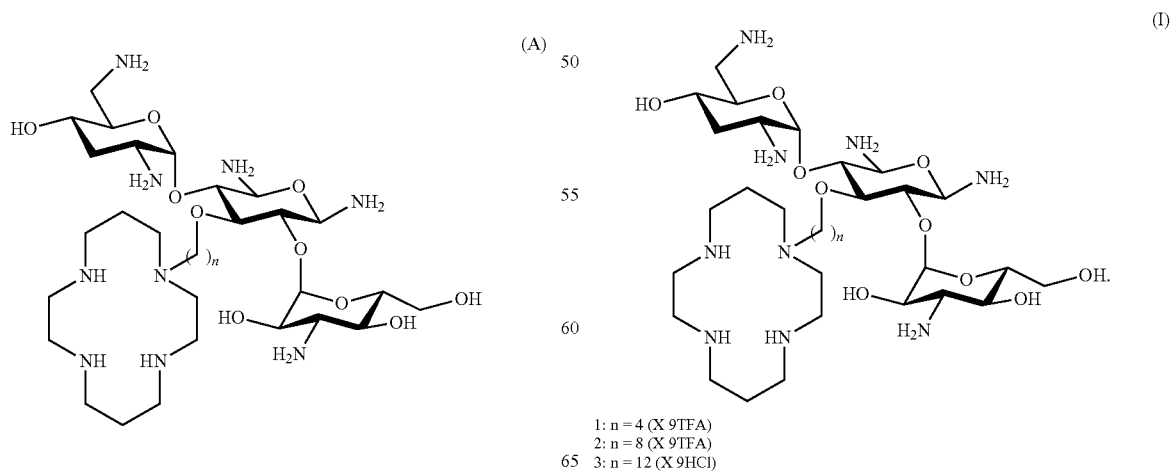

1: n = 4 (X 9TFA)
2: n = 8 (X 9TFA)
3: n = 12 (X 9HCl)

or a suitable salt form thereof, wherein ⌇ is a carbon tether having a length of between about 2-18 carbons.

3. The compound according to claim 1 consisting of a chemical structure or chemical formula of formula (I)

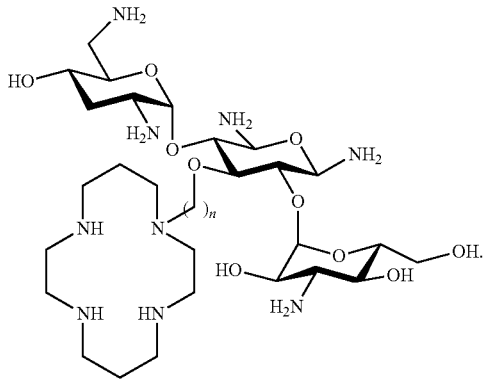

(I)

1: n = 4 (X 9TFA)
2: n = 8 (X 9TFA)
3: n = 12 (X 9HCl)

4. The compound according to claim 1 wherein the compound is an antibiotic adjuvant.

5. A method of perturbing or permeabilizing or destabilizing or increasing the fluidity or permeability of the outer membrane of a gram-negative bacterium comprising: administering to an individual in need of such treatment an effective amount of compound comprising a chemical structure of Formula (A), as set forth in claim 1.

6. The method according to claim 5 wherein the gram-negative bacterium is selected from the group consisting of: *Pseudomonas; Acetinobacter baumannii; E. coli; Klebsiella pneumoniae*; and Enterobacteriaceae.

7. The method according to claim 5 wherein the gram-negative bacterium is *Pseudomonas aeruginosa*.

8. The method according to claim 5 wherein the gram-negative bacterium is a multi-drug resistant bacterium (MDR), an extensively-drug resistant bacterium (XDR) or a pan-drug resistant bacterium (PDR).

9. The method according to claim 5 wherein the individual in need of such treatment is an individual who has, is known to have, has been diagnosed as having or is suspected of having a bacterial infection caused by a gram-negative bacterium.

10. The method according to claim 5 wherein the compound is co-administered with an effective amount of an antibiotic.

11. The method according to claim 10 wherein the antibiotic is selected from the group consisting of β-lactam antibiotics, β-lactam inhibitors and combinations thereof.

12. The method according to claim 11 wherein the β-lactam antibiotic is a monobactam, a penicillin, a cephalosporin or a carbapenem.

* * * * *